US012350410B2

(12) United States Patent
Childress

(10) Patent No.: US 12,350,410 B2
(45) Date of Patent: Jul. 8, 2025

(54) METHODS FOR CONTROLLING AIR DISINFECTING SYSTEMS

(71) Applicant: THE BOEING COMPANY, Chicago, IL (US)

(72) Inventor: Jamie J. Childress, Mercer Island, WA (US)

(73) Assignee: The Boeing Company, Chicago, IL (US)

(*) Notice: Subject to any disclaimer, the term of this patent is extended or adjusted under 35 U.S.C. 154(b) by 635 days.

(21) Appl. No.: 17/677,407

(22) Filed: Feb. 22, 2022

(65) Prior Publication Data

US 2023/0263926 A1 Aug. 24, 2023

(51) Int. Cl.
*A61L 9/20* (2006.01)
*A42B 3/28* (2006.01)

(52) U.S. Cl.
CPC ............... *A61L 9/20* (2013.01); *A42B 3/283* (2013.01); *A61L 2209/111* (2013.01); *A61L 2209/12* (2013.01)

(58) Field of Classification Search
CPC .. A61L 9/20; A61L 2209/111; A61L 2209/12; A61L 2209/134; A61L 2209/10;
(Continued)

(56) References Cited

U.S. PATENT DOCUMENTS

2004/0141875 A1* 7/2004 Doshi ................... B60H 3/06
422/4
2021/0361815 A1* 11/2021 Krosney ................. A61L 9/20

FOREIGN PATENT DOCUMENTS

| CA | 3115322 A1 | * | 10/2021 | ............. A41D 13/11 |
| WO | WO-2021211723 A1 | * | 10/2021 | ............... A23L 3/28 |
| WO | WO-2022040379 A1 | * | 2/2022 | ............. A61L 2/088 |

OTHER PUBLICATIONS

U.S. Appl. No. 17/016,466, filed Sep. 10, 2020.
(Continued)

*Primary Examiner* — Sean E Conley
*Assistant Examiner* — Aham Lee
(74) *Attorney, Agent, or Firm* — Joseph M. Butscher; The Small Patent Law Group, LLC

(57) ABSTRACT

A system and method include a duct including an internal air passage. One or more ultraviolet (UV) light emitters are coupled to the duct. The UV light emitter(s) are configured to emit UV light into air that passes through the internal air passage. An air inlet is coupled to the duct. The air inlet is in fluid communication with the internal air passage. An air outlet is coupled to the duct. The air outlet is in fluid communication with the internal air passage. A blower is disposed within the duct. The blower is configured to draw the air into the internal air passage through the air inlet, and discharge the air from the internal air passage through the air outlet. The air is disinfected within the internal air passage by the UV light emitted by the one or more UV lights. A sensor is coupled to one or more of the duct, the air inlet, or the air outlet. The sensor is configured to output signals. A control unit is in communication with the UV light emitter (s), the blower, and the sensor. The control unit is configured to receive the signals from the sensor and control one or both of the UV light emitter(s) or the blower based on the signals.

20 Claims, 22 Drawing Sheets

(58) Field of Classification Search
CPC ............... A61L 2209/14; A42B 3/283; B64D 2013/003; B64D 13/00; F24F 2221/38; F24F 8/22; F24F 11/0001
See application file for complete search history.

(56) References Cited

OTHER PUBLICATIONS

U.S. Appl. No. 29/735,235, filed May 19, 2020.
U.S. Appl. No. 17/039,011, filed Sep. 30, 2020.
U.S. Appl. No. 17/026,414, filed Sep. 21, 2020.
U.S. Appl. No. 17/020,942, filed Sep. 15, 2020.
U.S. Appl. No. 16/987,514, filed Aug. 7, 2020.
U.S. Appl. No. 17/104,628, filed Nov. 25, 2020.
U.S. Appl. No. 16/987,647, filed Aug. 7, 2020.
U.S. Appl. No. 17/026,417, filed Sep. 21, 2020.
U.S. Appl. No. 17/020,951, filed Sep. 15, 2020.
"Honeywell UV Treatment System," https://aerospace.honeywell.com/en/learn/products/cabin/uv-cabin-system.
U.S. Appl. No. 17/026,435, filed Sep. 21, 2020.
U.S. Appl. No. 17/022,392, filed Sep. 16, 2020.
U.S. Appl. No. 17/308,200, filed May 5, 2021.

* cited by examiner

METHODS FOR CONTROLLING AIR DISINFECTING SYSTEMS

FIELD OF THE DISCLOSURE

Examples of the present disclosure generally relate to systems and methods for disinfecting air, such as by ultraviolet (UV) light.

BACKGROUND OF THE DISCLOSURE

Aircraft are used to transport passengers and cargo between various locations. Passengers within an internal cabin of an aircraft can be seated in close proximity to one another.

Air within an internal cabin of an aircraft is typically a mixture of air exhaled by other passengers and fresh disinfected air. As can be appreciated, exhaled air can contain microbial particles, such as germs, bacteria, viruses, and the like.

SUMMARY OF THE DISCLOSURE

A need exists for a system and a method for efficiently and effectively disinfecting air, such as within a confined space (for example, an internal cabin of a vehicle).

With that need in mind, certain examples of the present disclosure provide a system including a duct including an internal air passage. One or more ultraviolet (UV) light emitters are coupled to the duct. The one or more UV light emitters are configured to emit UV light into air that passes through the internal air passage. An air inlet is coupled to the duct. The air inlet is in fluid communication with the internal air passage. An air outlet is coupled to the duct. The air outlet is in fluid communication with the internal air passage. A blower is disposed within the duct. The blower is configured to draw the air into the internal air passage through the air inlet, and discharge the air from the internal air passage through the air outlet. The air is disinfected within the internal air passage by the UV light emitted by the one or more UV light emitters. A sensor is coupled to one or more of the duct, the air inlet, or the air outlet. The sensor is configured to output signals. A control unit is in communication with the one or more UV light emitters, the blower, and the sensor. The control unit is configured to receive the signals from the sensor and control one or both of the one or more UV light emitters or the blower based on the signals.

In at least one example, the air inlet is in close proximity to the air outlet. In at least one example, the air inlet is disposed below the air outlet. In at least one example, the air inlet or the air outlet are configured to be disposed one or both of below or in front of a mouth of an individual. The air outlet is configured to discharge disinfected air upwardly toward the mouth to provide an air curtain in front of a face the individual.

In at least one example, the sensor is a microphone, and the signals are audio signals.

In at least one example, the control unit is configured to determine a breathing rate of an individual based on the signals.

In at least one example, the control unit is configured to control both the one or more UV light emitters and the blower based on the signals.

In at least one example, the control unit is configured to increase power to one or both of the one or more UV light emitters or the blower when the signals indicate that an individual is or is about to inhale air discharged from the air outlet, and the control unit is configured to decrease power to one or both of the one or more UV light emitters or the blower when the signals indicate that the individual is not or is not about to inhale air discharged from the air outlet.

The system can also include a power source that supplies power to the one or more UV light emitters, the blower, the control unit, and the sensor.

In at least one example, the duct, the air inlet, the air outlet, and the control unit are coupled to a helmet.

Certain examples of the present disclosure provide a method including emitting, by one or more ultraviolet (UV) light emitters coupled to a duct including an internal passage, UV light into air that passes through the internal air passage; drawing, by a blower coupled to the duct, the air into the internal air passage through an air inlet; discharging, by the blower, the air from the internal air passage through an air outlet; outputting, by a sensor coupled to one or more of the duct, the air inlet, or the air outlet, signals; receiving, by a control unit in communication with the one or more UV light emitters, the blower, and the sensor, the signals from the sensor; and controlling, by the control unit, one or both of the one or more UV light emitters or the blower based on the signals.

DETAILED DESCRIPTION OF THE DISCLOSURE

The foregoing summary, as well as the following detailed description of certain examples will be better understood when read in conjunction with the appended drawings. As used herein, an element or step recited in the singular and preceded by the word "a" or "an" should be understood as not necessarily excluding the plural of the elements or steps. Further, references to "one example" are not intended to be interpreted as excluding the existence of additional examples that also incorporate the recited features. Moreover, unless explicitly stated to the contrary, examples "comprising" or "having" an element or a plurality of elements having a particular condition can include additional elements not having that condition.

Air within an internal cabin of a vehicle, such as a commercial aircraft, may need additional disinfection to provide reduced active microbial particles and to increase passenger sense of well-being. Ultraviolet (UV) light can be used to neutralize microbial pathogens, such as bacteria, germs, viruses, and the like. However, shining an ultraviolet (UV) light directly on the face of an individual may not be possible at sufficient irradiance to neutralize pathogens. Examples of the present disclosure provide systems and methods that direct air flow around the face of an individual. The air flow is disinfected using UV light. One or more UV light emitters are contained in an enclosure that disinfects the air just prior to emission near the face of the individual. The UV light within the enclosure can be reflected, thereby increasing the UV exposure of the air.

In at least one example, the system includes an assembly that can be worn by an individual. As another example, the assembly can be mounted to a structure, such as a headrest of a seat. The UV light emitters can be UV light emitting diodes (LEDs), which generate minimal or low ozone. In at least one example, the system includes a UV reflective duct section supporting UV LED strips for disinfection, and UV absorbing sections, such as an at an air inlet and air outlet to prevent or otherwise reduce escape of UV light. The system can also include a blower, such as a fan, which draws air into and through the duct, and out of the air outlet. Further, the air inlet can be larger than the air outlet, thereby providing increased air velocity at the outlet (such as toward an individual's face). The air inlet can be in close proximity to the air outlet. As such, the blower can draw air into the duct from near an individual's face when exhaling, and the system can clean the air and provide it near the intake area.

Figure 1:
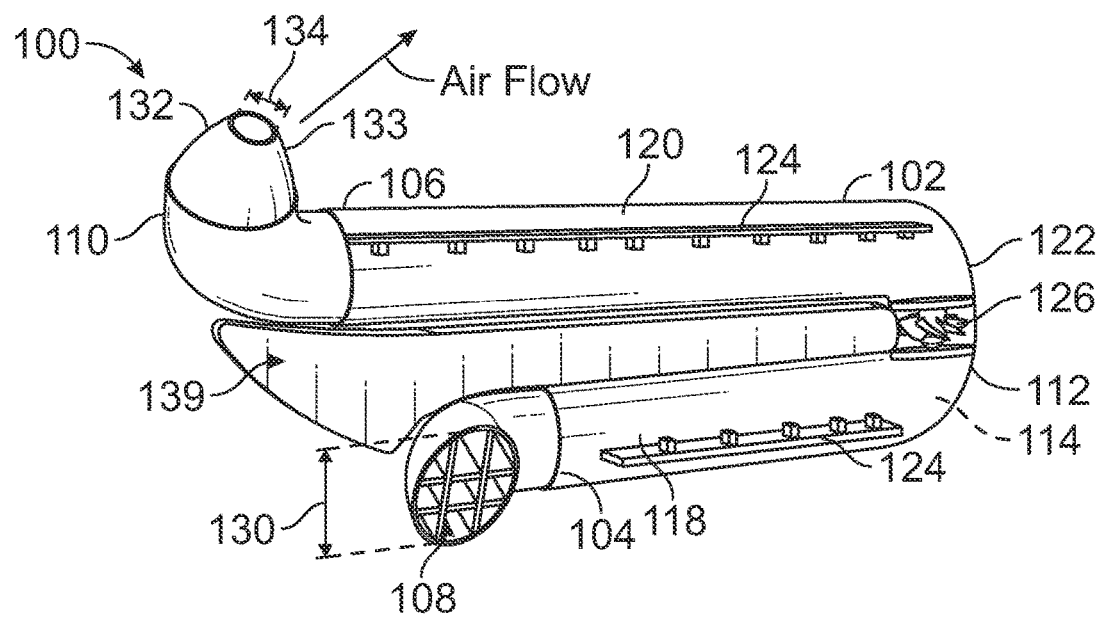
FIG. 1 illustrates an isometric view of a system for disinfecting air, according to an example of the present disclosure.

FIG. 1 illustrates an isometric view of a system 100 for disinfecting air, according to an example of the present disclosure. The system 100 includes a duct 102 having an inlet end 104 and an outlet end 106. An air inlet 108 is disposed at the inlet end 104, and an air outlet 110 is disposed at the outlet end 106.

The duct 102 is a tube, pipe, or other such conduit that includes an outer wall 112 that defines an internal air passage

114. The internal air passage 114 provides an internal path for air to travel between the inlet end 104 and the outlet end 106, and therefore the air inlet 108 and the air outlet 110. The air inlet 108 is in fluid communication with the air outlet 110 through the internal air passage 114 of the duct 102.

As shown, the duct 102 includes a first segment 118 connected to a second segment 120 through a bend 122. The first segment 118 can be a straight, linear segment. Similarly, the second segment 120 can be a straight, linear segment. The bend 122 can provide a 180 degree turn so that the first segment 118 and the second segment 120 are generally parallel with one another. By providing a 180 degree turn, the bend 122 allows the air inlet 108 to be in close proximity to the air outlet 110. As such, the bend 122 positions the air outlet 110 proximate to the air inlet 108. For example, the air inlet 108 can be within 6 inches or less of the air outlet 110. Optionally, the duct 102 can include more bends than shown. Further, the bend 122 can be less than 180 degrees. As another example, the duct 102 may not include any bend. Instead, the air inlet 108 and the air outlet 110 can be at opposite ends of a straight duct.

One or more ultraviolet (UV) light emitters 124 (or UV lights) are coupled to a duct 102. For example, the UV light emitters 124 can be disposed within the duct 102. As another example, at least portions of the UV light emitters 124 can be outside of the duct 102. As an example, the UV light emitters 124 can protrude into openings formed in the duct 102. The UV light emitters 124 can be secured to portions of the duct 102 through one or more fasteners, adhesives, or the like. For example, a plurality of UV light emitters 124 are disposed within the internal air passage 114 within the first segment 118, and a plurality of UV light emitters 124 are disposed within the internal passage 114 within the second segment 118. Optionally, UV light emitters 124 can be disposed within the bend 122. As another example, one or more UV light emitters 124 are disposed within the one of the first segment 118, the second segment 120, or the bend 122. As another example, one or more UV light emitters 124 are disposed within each of the first segment 118, the second segment 120, and the bend 122.

The UV light emitters 124 are configured to emit UV light into air that passes through the duct 102, thereby disinfecting the air as it passes from the air inlet 108 and to and through the air outlet 110. In at least one example, the UV light emitters 124 are configured to emit UV light at a wavelength ranging from 270-280 nanometers (nm). Optionally, the UV light emitters 124 can be configured to emit UV light at different wavelengths, such as ranging from 210-230 nm, 240-260 nm, and/or the like.

The duct 102 is formed of (or has internal portions formed of or coated with) a reflective material. For example, the duct 102 is formed of aluminum. In another example, the duct 102 can be formed of Teflon. Internal surfaces of the duct 102 that define the internal air passage 114 are formed of, or otherwise coated, with a reflective material, such as aluminum, or Teflon. Outer surfaces of the outer wall 112 are formed of, or otherwise coated with an opaque material, such as a metal, thereby ensuring that UV light emitted by the UV light emitters 124 does not escape out and through the outer wall 112 of the duct 102. In this manner, the duct 102 is a light pipe that internally reflects UV light emitted by the UV light emitters 124 but prevents the UV light from escaping through the outer wall 112.

The air inlet 108 and the air outlet 110 are formed of UV absorbing material. For example, the air inlet 108 and the air outlet 110 are formed of a dark plastic, which absorbs UV light, thereby eliminating, minimizing, or otherwise reducing the potential of UV light escaping therethrough. For example, the air inlet 108 and the air outlet 110 can be formed of dark, opaque plastic. In at least one example, the air inlet 108 and the air outlet 110 can be black plastic. The darker the plastic, the more UV light will be absorbed.

A blower 126, such as a fan, is coupled to the duct 102. For example, the blower 126 can be disposed within the duct 102. As another example, the blower 126 can have a portion disposed within the duct 102, and another portion outside of the duct 102. As another example, the duct 102 can have an opening into which a conduit that connects to the blower 126 is secured. The blower 126 can be secured within the duct 102 through one or more fasteners, adhesives, and/or the like. As an example, the blower 126 is disposed within the bend 122. Optionally, the blower 126 can be disposed within the first segment 118 or the second segment 120. As another example, additional blowers 126 can be disposed within one or more portions of the duct 102.

The air inlet 108 has a first diameter 130 that defines an opening through which air is drawn into the duct 102. The air outlet 110 has a conic body 132 having a nozzle 133 defining a second diameter 134, which is substantially smaller than the first diameter 130. The second diameter 134 defines an opening through which air is discharged from the system 100. For example, the second diameter 134 can be half or less than the first diameter 130. As another example, the second diameter 134 is a quarter or less than the first diameter 130. By reducing the size of the second diameter 134 of the air outlet 110 in relation to the first diameter 130 of the air inlet 108, air discharged through the air outlet 110 is at increased velocity as compared to air that is drawn in through the air inlet 108. Optionally, the second diameter 134 of the air outlet 110 may not be substantially smaller than the first diameter 130 of the air inlet 108. For example, the first diameter 130 and the second diameter 134 can be alternatively equal to one another.

In at least one example, a support insert 139, such as a bracket, block, or the like, is secured between the first segment 118 and the second segment 120. The support insert 139 ensures that the first segment 118 and the second segment 120 do not undesirably encroach upon one another. Optionally, the system 100 may not include the support insert 139.

Figure 2:
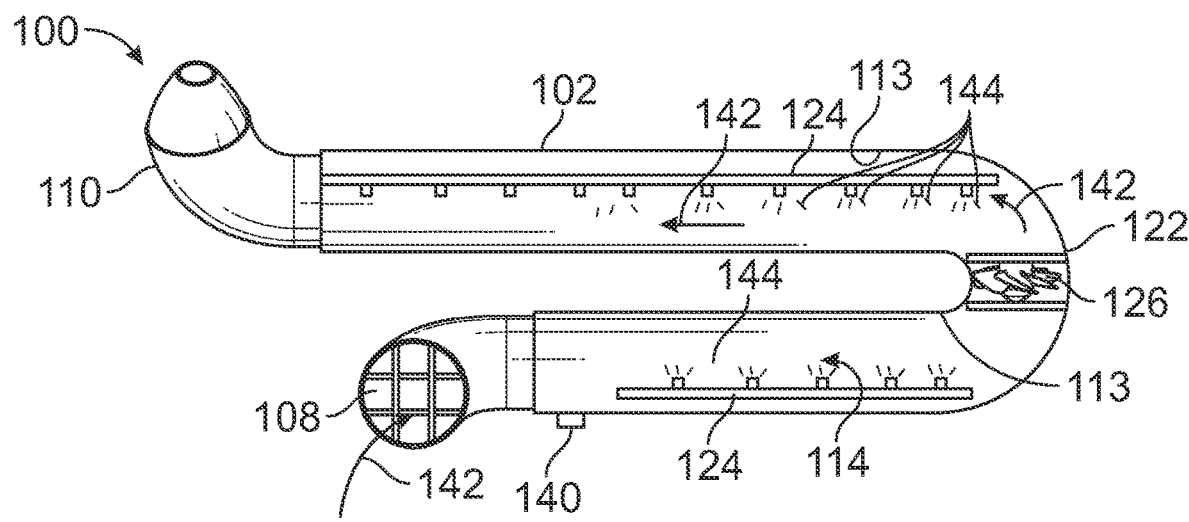
FIG. 2 illustrates an internal view of the system for disinfecting air.

FIG. 2 illustrates an internal view of the system 100 for disinfecting air. Referring to FIGS. 1 and 2, the system 100 can include an activation switch 140 that is in communication with the UV light emitters 124 and the blower 126, such as through one or more wired or wireless connections. The activation switch 140 can be mounted on and/or within the duct 102, the air inlet 108, or the air outlet 110. Optionally, the activation switch 140 can be remotely located from the duct 102, the air inlet 108, or the air outlet 110. For example, the activation switch 140 can be mounted to a portion of a seat.

When the switch 140 is in an ON position, the UV light emitters 124 are activated to emit the UV light, and the blower 126 is activated to draw air into the duct 102 through the air inlet 108, and out through the air outlet 110. When the switch 140 is in an OFF position, the UV light emitters 124 and the blower 126 are deactivated. The switch 140 can be a or otherwise include a physical switch, such as a button, key, dial, toggle, or the like that is configured to be selectively engaged by an individual between the ON and OFF positions. Optionally, the switch 140 can be or include a sensor that is configured to automatically activate and deactivate the UV light emitters 124 and the blower 126. For example, the sensor can be a motion or fluid sensor that detects individual motion, fluid flow, and/or the like.

In operation, the blower 126 is activated to draw air 142 into the duct 102 through the air inlet 108. The blower 126 can be configured to move the air 142 within the internal air passage 114 of the duct 102 at a relatively low velocity to ensure that the air 142 is exposed to the UV light 144 for a sufficient amount of time to disinfect the air 142. The smaller diameter 134 of the air outlet 110 ensures that the disinfected air 142 is expelled at a higher velocity than air is drawn in through the air inlet 108. As such, the reduced diameter nozzle 133 increases the velocity of disinfected air that is expelled out of the system 100 (such as onto a face of an individual). At the same time, the larger diameter of the internal air passage 114 limits the velocity of air flowing therein, which increases the amount of time the air 142 is exposed to the UV light 144 emitted and reflected within the duct 102. As an example, the diameter of the air inlet 108 and the internal air passage 114 can range from 1-2 inches, while the diameter of the nozzle 133 can range from 0.1-0.5 inches.

As the air passes through the internal air passage 114, the UV light emitters 124 emit UV light 144 into the flowing air 142, thereby disinfecting the air 142. The emitted UV light 144 internal reflects off the internal reflective surfaces of the duct 102 (such as a light pipe), thereby continually passing into and through the air 142, which provides increased and efficient disinfection of the air 142. The UV light within the duct 102 is continually internally reflected, thereby increasing the air to increased UV exposure. The blower 126 moves the air through the internal air passage 114 toward the air outlet 110, with the UV light emitters 124 emitting the UV light 144 into the air 142 between the air inlet 108 and the air outlet 110 to disinfect the air 142 (for example, neutralize microbial pathogens, such as germs, bacteria, viruses, and the like). Because the air inlet 108 and the air outlet 110 are formed of UV absorbing material (such as a dark plastic), the potential of UV light escaping out of the system 100 is eliminated, minimized, or otherwise reduced.

The duct 102 provides a path for air to pass through, and be disinfected by UV light emitted from the UV light emitters 124 and internally reflected within the duct 102. The duct 102 can provide a circuitous path that ensures that the air 142, as moved by the blower 126, is exposed to UV light for a sufficient amount of time to disinfect the UV light (for example, neutralize any pathogens contained therein). The air 142 is disinfected by the UV light emitted by the UV light emitters 124 before being discharged through the air outlet 110.

In at least one example, the UV light 144 emitted by the UV light emitters 124 is selected to have low ozone emission into an air stream (for example, UV LEDs that emit UV light at a wavelength of 222 nm). Any UV light that escapes the system 100 is sufficiently low that long duration passenger exposure is within allowable limits as defined by regulatory agencies (such as the Federal Aviation Administration). The UV light 144 within the duct 102 is reflected many times from internal reflective surfaces 113 that define the internal air passage 114, thereby increasing the UV exposure of the air. For example, the internal reflective surfaces 113 can be formed of or otherwise coated with Teflon, which has approximately 96% reflectivity at UV frequencies allowing high UV irradiance along the internal air passage 114.

The bend 122 disposes the air inlet 108 proximate to the air outlet 110. As such, both the air inlet 108 and the air outlet 110 can be disposed close to a face of an individual, thereby ensuring the air exhaled by an individual is drawn into the duct 102, disinfected as described herein, and expelled for the individual to breathe.

The system 100 provides disinfected air while consuming less power as compared to a UV light that is configured to direct UV light directly onto a face of an individual. Further, the system 100 eliminates, minimizes, or otherwise reduces UV exposure to skin and eyes of an individual. The system 100 also provides increased disinfection of air next to an individual's face. Also, the blower 126 is configured to consume a relatively small amount of power and move air at a relatively low velocity, thereby decreasing operational costs, and reducing generated noise.

The system 100 can be worn by an individual. For example, the system 100 can include a clip, hook, loop, or the like that allow an individual to wear the system 100. As another example, the system 100 can be secured to a structure, such as headrest of a seat, such as within a vehicle (for example, a commercial aircraft), or within a venue such as a theater, stadium, or the like.

As described herein, the system 100 includes the duct 102 including the internal reflective surfaces 113 surrounding at least a portion of the internal air passage 114. One or more ultraviolet (UV) lights 124 are disposed within the duct 102. The one or more UV lights 124 are configured to emit UV light 144 into the air 142 that passes through the internal air passage 114. The internal reflective surfaces 113 reflect the UV light 144 within the internal air passage 114. The air inlet 108 is coupled to the duct, 102. The air inlet 108 is in fluid communication with the internal air passage 114. The air outlet 110 is coupled to the duct 102. The air outlet 110 is in fluid communication with the internal air passage 114. The blower 126 is disposed within the duct 102. The blower 126 is configured to draw air 142 into the internal air passage 114 through the air inlet 108, and discharge the air 142 from the internal air passage 114 through the air outlet 110. The air 142 is disinfected within the internal air passage 114 by the UV light 144 emitted by the one or more UV lights 124 and reflected by the internal reflective surfaces 113.

Figure 3:
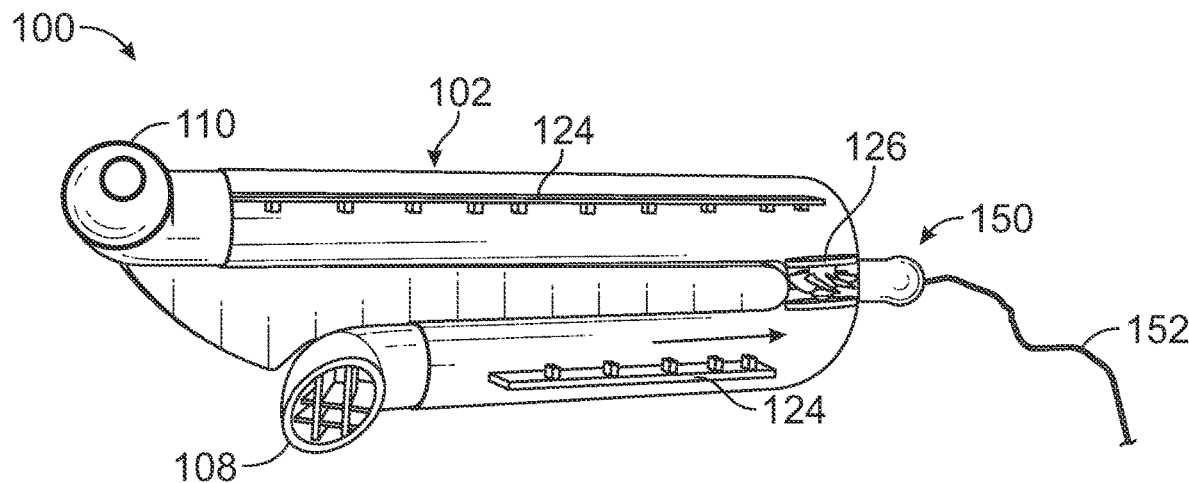
FIG. 3 illustrates an isometric view of the system for disinfecting air, according to an example of the present disclosure.

FIG. 3 illustrates an isometric view of the system 100 for disinfecting air, according to an example of the present disclosure. As shown, the system 100 can include a mounting member 150, which is configured to secure the system 100 to a structure, such as headrest of a seat. The mounting member 150 can be a clamp, bracket, or the like. In at least one example, the mounting member 150 is or otherwise includes a ball pivot, hinge, swivel, or the like. A power line 152 (such as a cable or wire) connects to the blower 126 and the UV light emitters 124. The power line 152 provides electrical power from a power source to the blower 126 and the UV light emitters 124. Optionally, the system 100 can include an internal source of power, such as one or more batteries.

Figure 4:
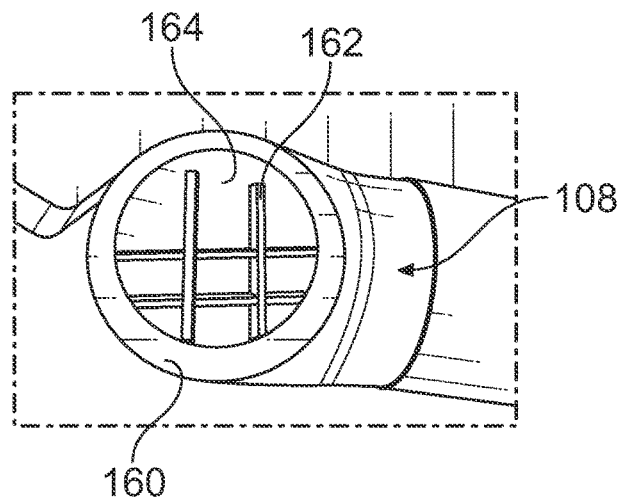
FIG. 4 illustrates a front view of an air inlet, according to an example of the present disclosure.

FIG. 4 illustrates a front view of the air inlet 108, according to an example of the present disclosure. In at least one example, the air inlet 108 includes a plurality of intersecting fins 162 disposed within an internal channel 164. The fins 162 can be flat panels formed of a UV light absorbing material, such as a plastic. Air is drawn into the air inlet 108 through the internal channel 164, while the fins 162 provide an additional barrier that absorbs UV light and prevents the UV light from passing out of the air inlet 108. The air outlet 110 (shown in FIGS. 1-3) can also include fins as shown and described with respect to FIG. 4. The fins 162 provide low air flow resistance, and high UV light absorption.

Figure 5:
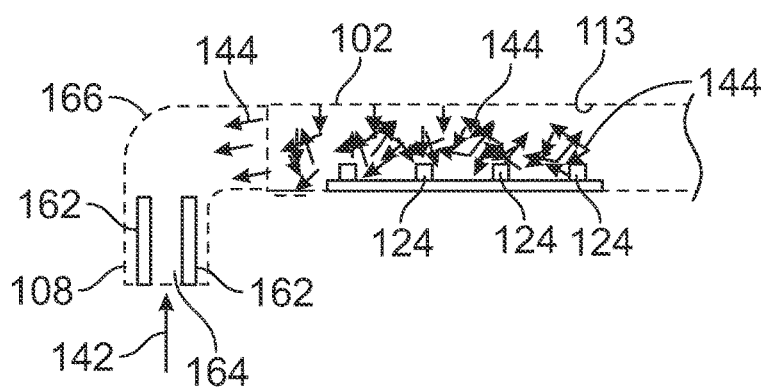
FIG. 5 illustrates a simplified internal view of the system for disinfecting air, according to an example of the present disclosure.

FIG. 5 illustrates a simplified internal view of the system for 100 disinfecting air, according to an example of the present disclosure. The air inlet 108 can include a bend 166 that leads to the duct 102. The fins 162 extend into the air inlet 108 toward the bend 166. The fins 162 provide barriers that block UV light 144 from escaping through the air inlet 108. As the UV light 144 impinges on the fins 162, the UV light is absorbed by the fins 162. The air 142 is drawn in through the air outlet and into the duct 102, such as by the blower 126 (shown in FIGS. 1-3).

As shown, the internal reflective surfaces 113 of the duct 102 internally reflect the UV light 144 emitted by the UV light emitters 124. Accordingly, the duct 102 provides a light pipe that is configured to internally reflect the UV light 144.

Figure 6:
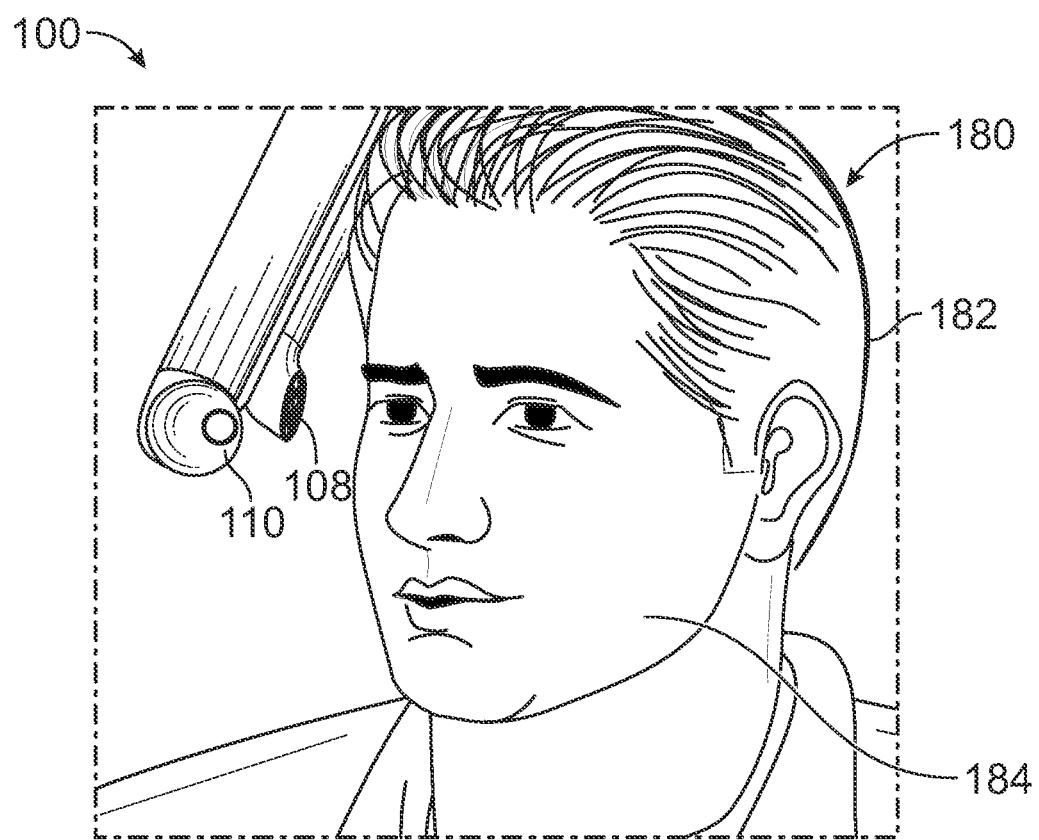
FIG. 6 illustrates an isometric view of the system for disinfecting air in relation to an individual, according to an example of the present disclosure.

FIG. 6 illustrates an isometric view of the system 100 for disinfecting air in relation to an individual 180, according to an example of the present disclosure. In at least one example, the individual 180 wears the system 100. For example, the system 100 can include a clip, hook, loop, or the like that allows the system 100 to be worn on a head 182. As another example, the system 100 can be secured to a headrest of a seat on which the individual 180 is seated.

As described above, the air inlet 108 and the air outlet 110 can be in closed proximity to one another. Referring to FIGS. 1-6, the bend 122 orients the first segment 118 and the segment 120 to be substantially parallel (such as within 5 degrees), which allows the air inlet 108 to be in close proximity (such as within 6 inches) to the air outlet 110.

The UV light emitters 124 emit the UV light 144, which allows local air surrounding the individual 180 to be disinfected within the duct 102, which provides a circuitous loop and light pipe. The blower 126 draws air from near the face 184 of the individual in through the air inlet 108. The air is disinfected by UV light 144 emitted by the UV light emitters 124 and internally reflected within the duct 102. The disinfected air is then discharged through the air outlet 110 near the face 184. Because the disinfection of the air is highly localized, even aerosolized pathogens from an individual sitting next to the individual 180 will be neutralized.

Figure 7:
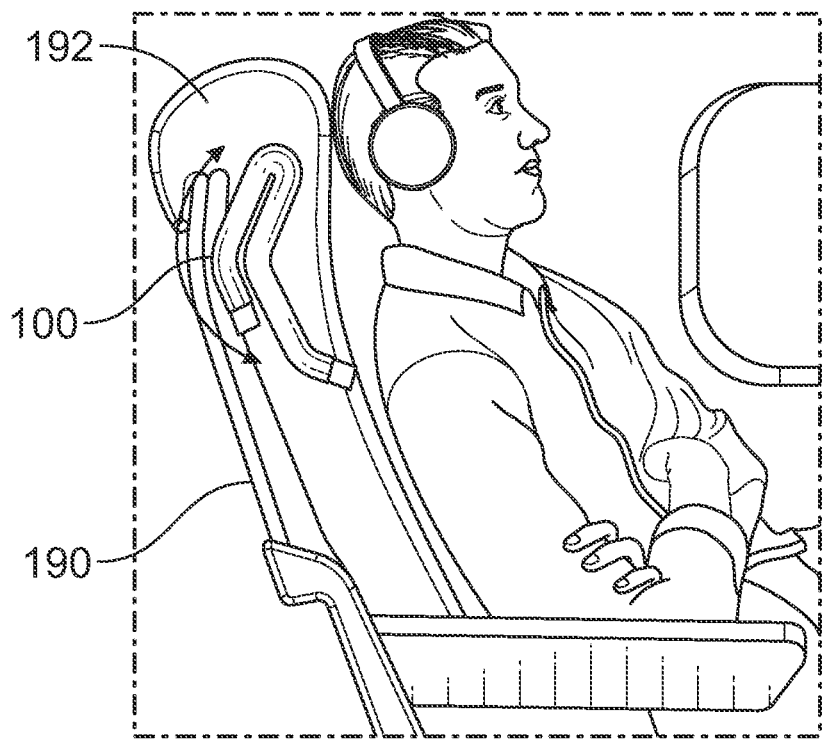
FIG. 7 illustrates a side view of the system for disinfecting air in a stowed position on a seat, according to an example of the present disclosure.

FIG. 7 illustrates a side view of the system 100 for disinfecting air in a stowed position on a seat 190, according to an example of the present disclosure. Referring to FIGS. 1-3 and 7, the mounting member 150 secures the system 100 to a portion of the seat 190, such as to a side portion of a headrest 192. The mounting member 150 can be a pivoting structure, such as a ball pivot, which allows the system 100 to rotate about an axis.

Figure 8:
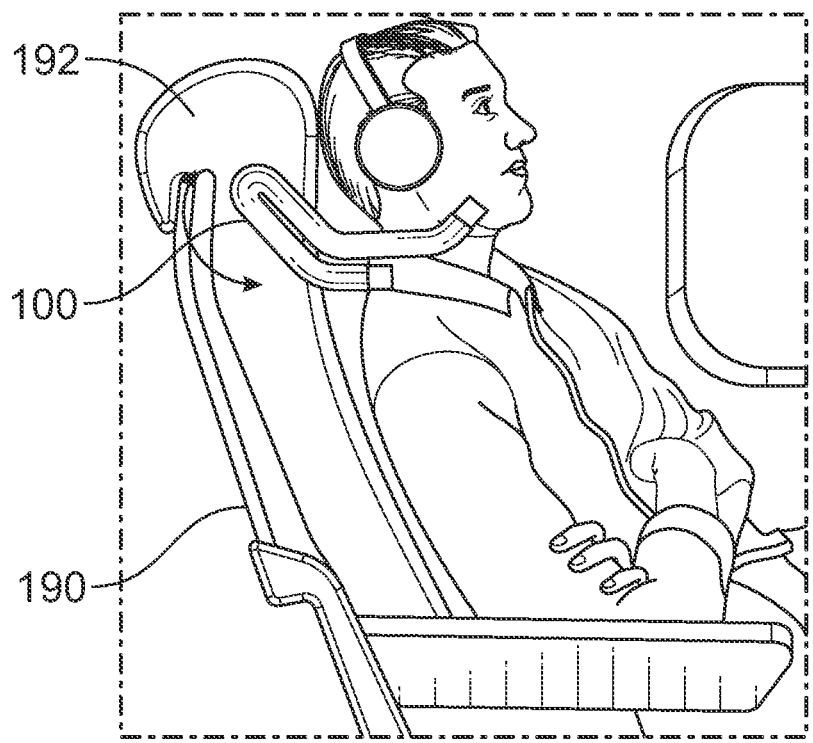
FIG. 8 illustrates a side view of the system for disinfecting air in a deployed position on the seat.

FIG. 8 illustrates a side view of the system 100 for disinfecting air in a deployed position on the seat 190. An individual can pivot the system 100 between the stowed position (shown in FIG. 7) and the deployed position, such as about the mounting member 150.

Figure 9:
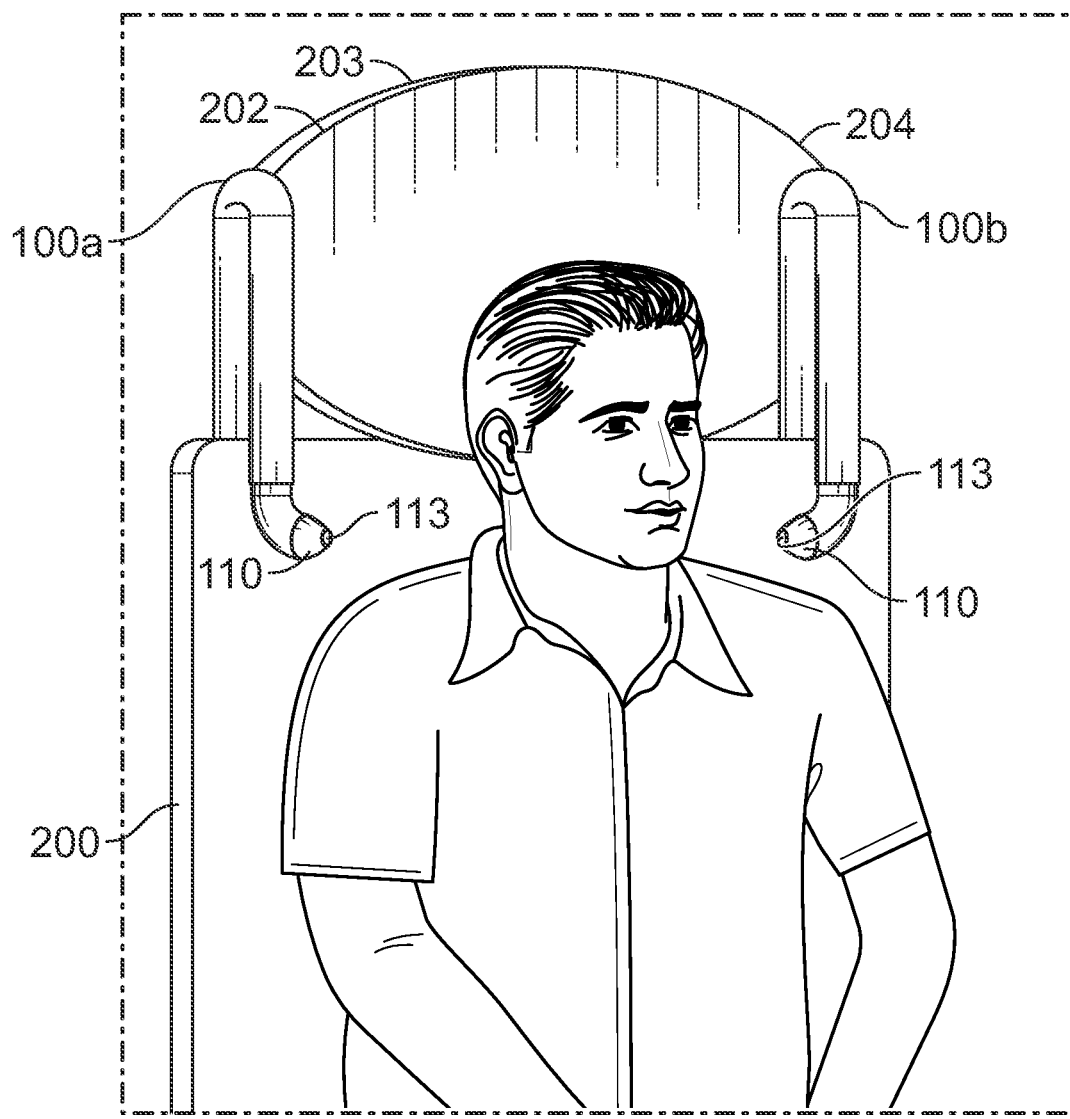
FIG. 9 illustrates a front view of a seat having a first system for disinfecting air and a second system for disinfecting air, according to an example of the present disclosure.

FIG. 9 illustrates a front view of a seat 200 having a first system 100a for disinfecting air and a second system 100a for disinfecting air, according to an example of the present disclosure. The first system 100a and the second system 100b are configured as any of the systems 100 described herein. The first system 100a is secured to a first side 202 of a headrest 203, and the second system 100b is secured to a second side 204 of the headrest 203. The second side 204 is opposite from the first side 202. The first system 100a and the second system 100b can be fixed in position. Optionally, the first system 100a and the second system 100b can be moveably coupled to the headrest 203 and configured to be moved between stowed and deployed positions.

In at least one example, the air outlets 110 can be fixed in position. In at least one other example, the nozzle 133 is movable. For example, the nozzle 133 can be pivotally mounted to allow for rotation to desired positions. Any of the examples described herein can include moveable nozzles 133.

Figure 10:
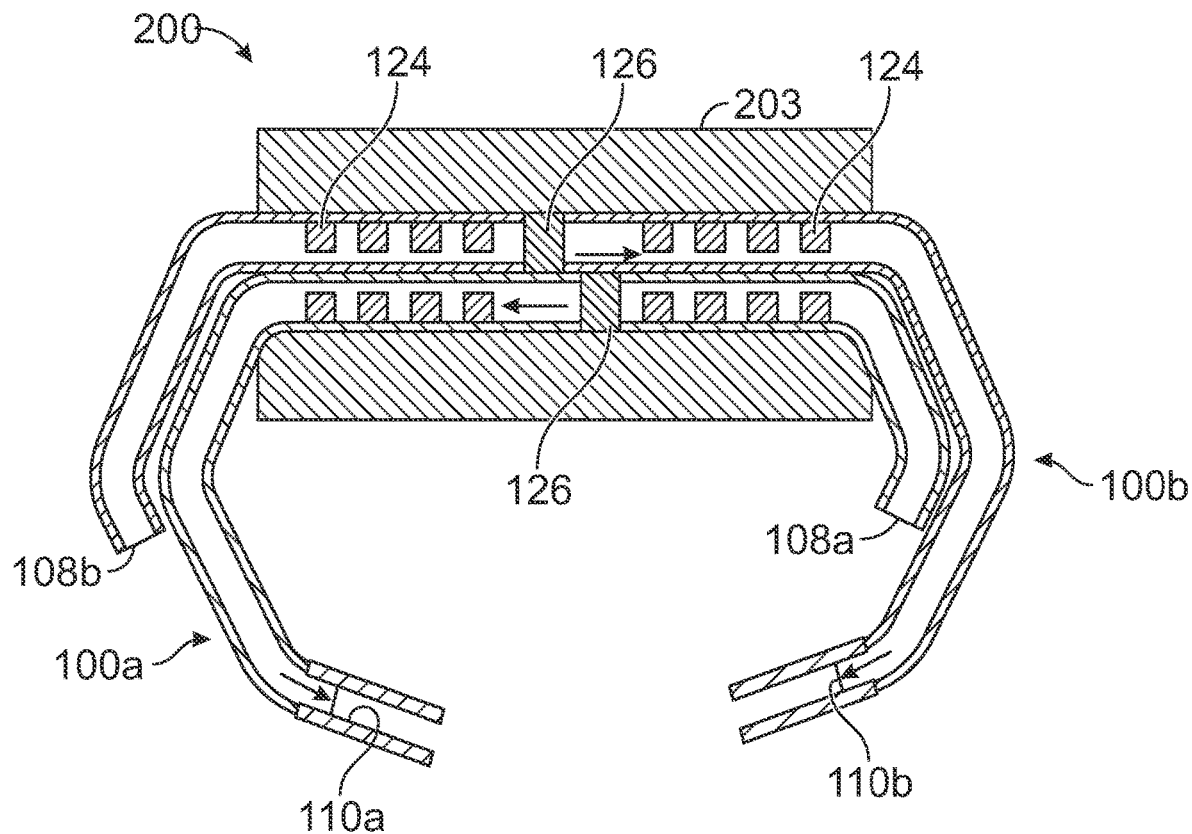
FIG. 10 illustrates a simplified internal view of a headrest of a seat having the first and second systems, according to an example of the present disclosure.

FIG. 10 illustrates a simplified internal view of the headrest 203 of the seat 200 having the first and second systems 100a and 100b, according to an example of the present disclosure. As shown, ducts 102 of the systems 100a and 100b can pass through internal portions of the headrest 203. The ducts 102 can be fixed within the headrest 203.

Figure 11:
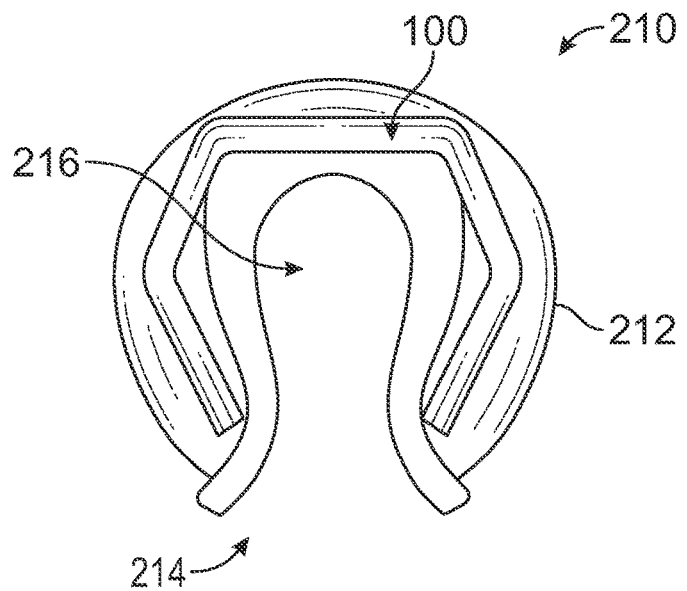
FIG. 11 illustrates a top view of a pillow including a system for disinfecting air, according to an example of the present disclosure.

FIG. 11 illustrates a top view of a pillow 210 including the system 100 for disinfecting air, according to an example of the present disclosure. The pillow 210 can be a neck pillow having an arcuate main body 212 defining an opening 214 that leads into a neck cavity 216. The pillow 210 can be configured to be worn around a neck of an individual. The system 100, such as any of those described herein, can be incorporated into the pillow 210. For example, the system 100 can be mounted on a portion of the main body 212. As another example, the system 100 can be disposed within at least a portion of the main body 212. Accordingly, the system 100 can be incorporated into the pillow 210.

Figure 12:
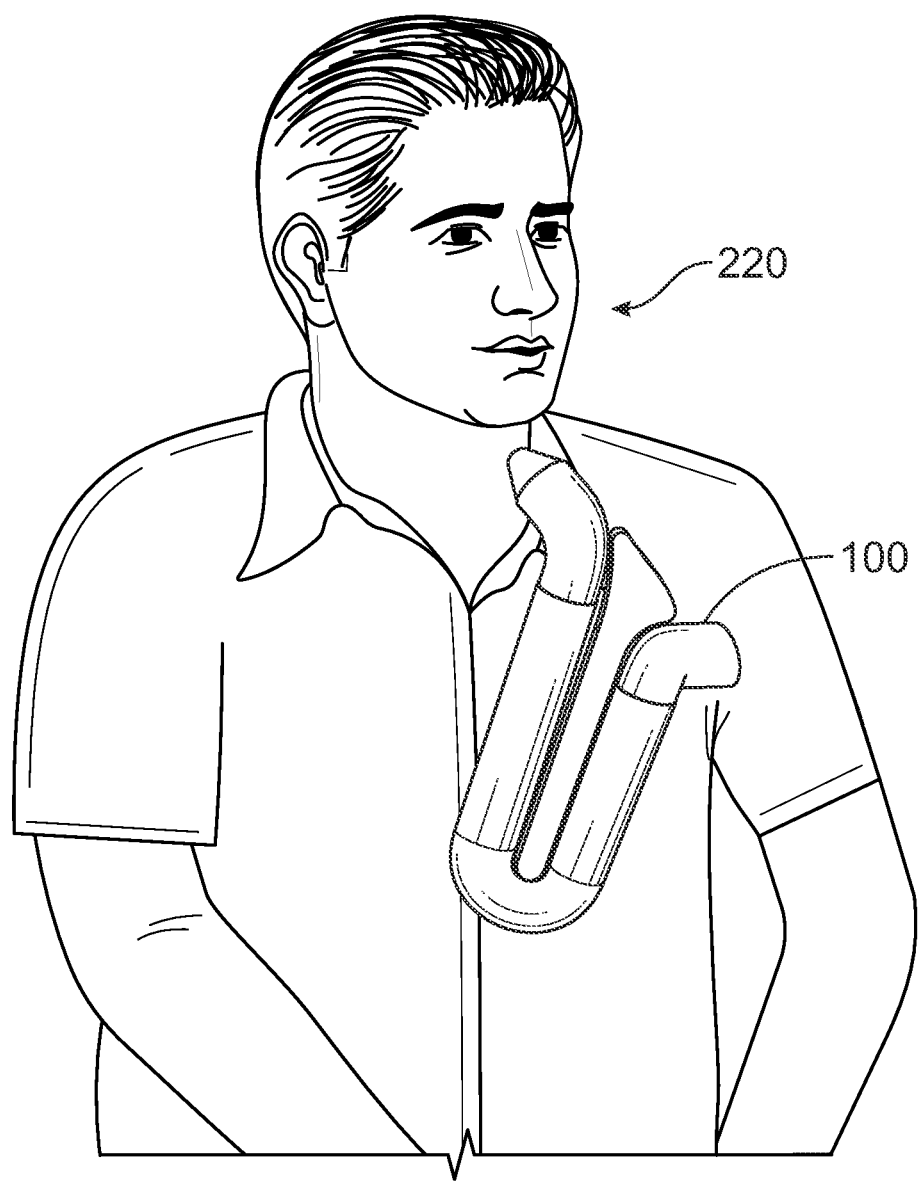
FIG. 12 illustrates an isometric front view of a system for disinfecting air worn by an individual, according to an example of the present disclosure.

FIG. 12 illustrates an isometric front view of the system 100 for disinfecting air worn by an individual 220, according to an example of the present disclosure. The system 100, such as any of those described herein, can include one or more straps, hooks, loops, or the like that allow the individual 220 to wear the system 100 over a chest. In another example, the system 100 can be worn on a head of the individual.

Figure 13:
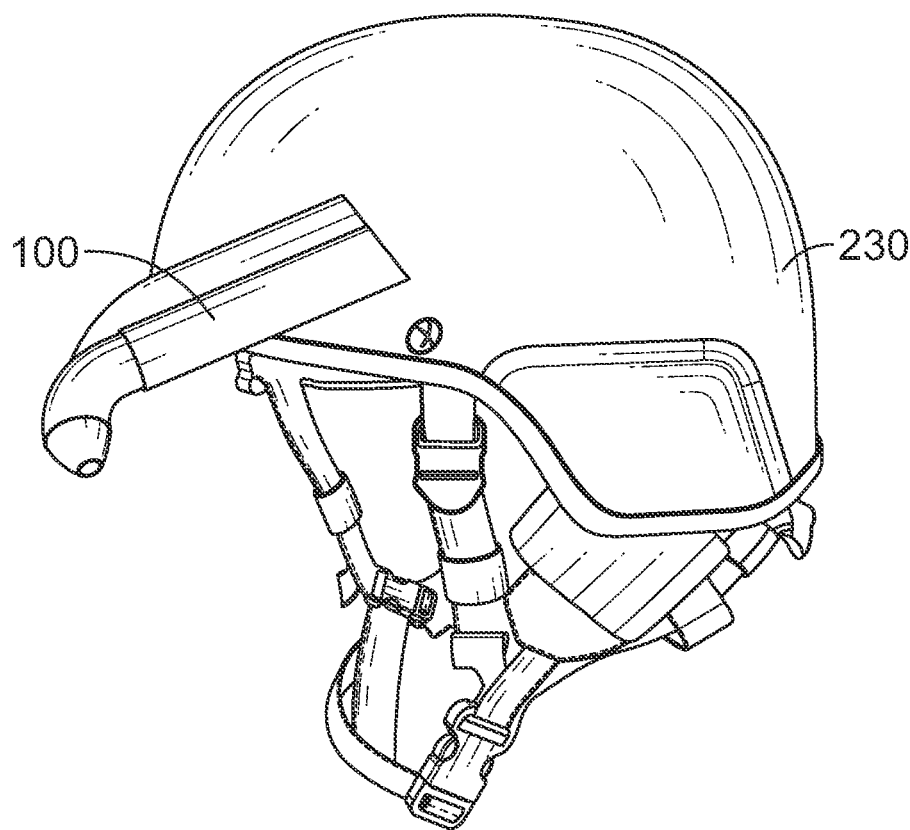
FIG. 13 illustrates a side view of a helmet including a system for disinfecting air, according to an example of the present disclosure.

FIG. 13 illustrates a side view of a helmet 230 including a system 100 for disinfecting air, according to an example of the present disclosure. The system 100, such as any of those described herein, can be secured to a portion of the helmet 230, such as an outer or interior portion of the helmet 230. As such, the system 100 can be incorporated into the helmet 230.

Figure 14:
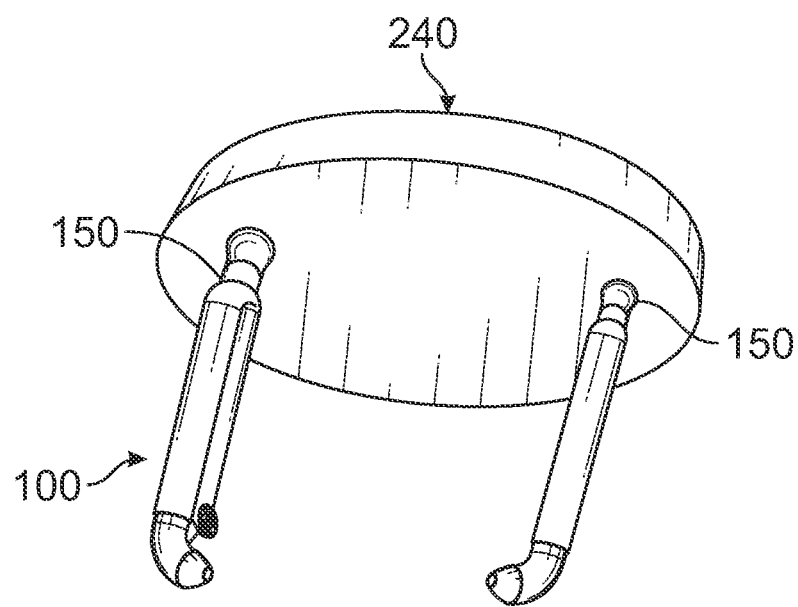
FIG. 14 illustrates an isometric front view of a headrest including systems for disinfecting air in deployed positions, according to an example of the present disclosure.

FIG. 14 illustrates an isometric front view of a headrest 240 including systems 100a and 100b for disinfecting air in deployed positions, according to an example of the present disclosure. The systems 100a and 100b can be configured as any of the systems 100 described herein. The systems 100a and 100b moveably couple to the headrest 240 through the mounting members 150, which can be pivot joints.

Figure 15:
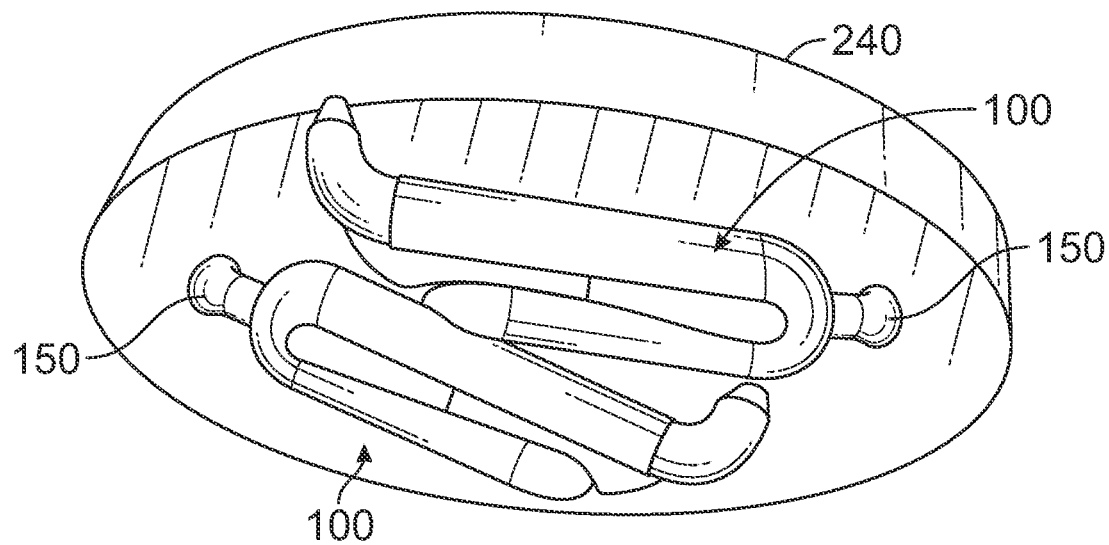
FIG. 15 illustrates an isometric front view of the headrest of FIG. 14 having the systems in stowed positions.

FIG. 15 illustrates an isometric front view of the headrest 240 of FIG. 14 having the systems in stowed positions. As shown, the systems 100a and 100b can outwardly pivot to deployed positions, as shown in FIG. 14, and inwardly pivot across the headrest 203 to stowed positions.

Figure 16:
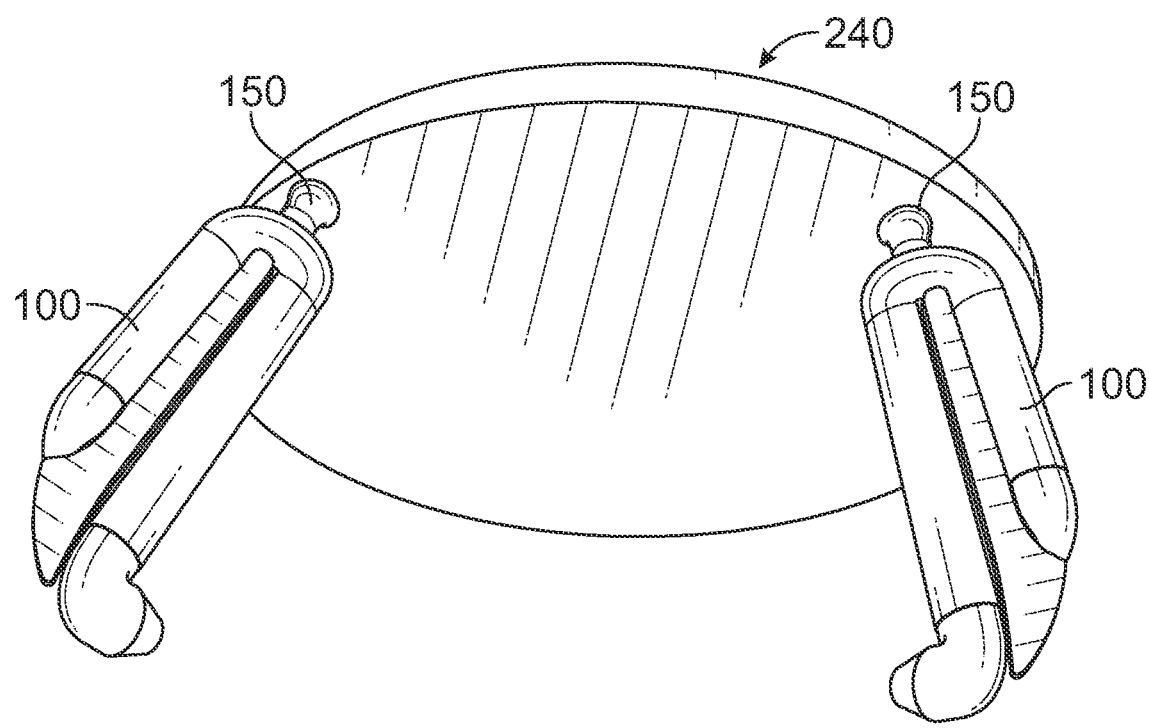
FIG. 16 illustrates an isometric front view of a headrest including systems for disinfecting air in deployed positions, according to an example of the present disclosure.
Figure 17:
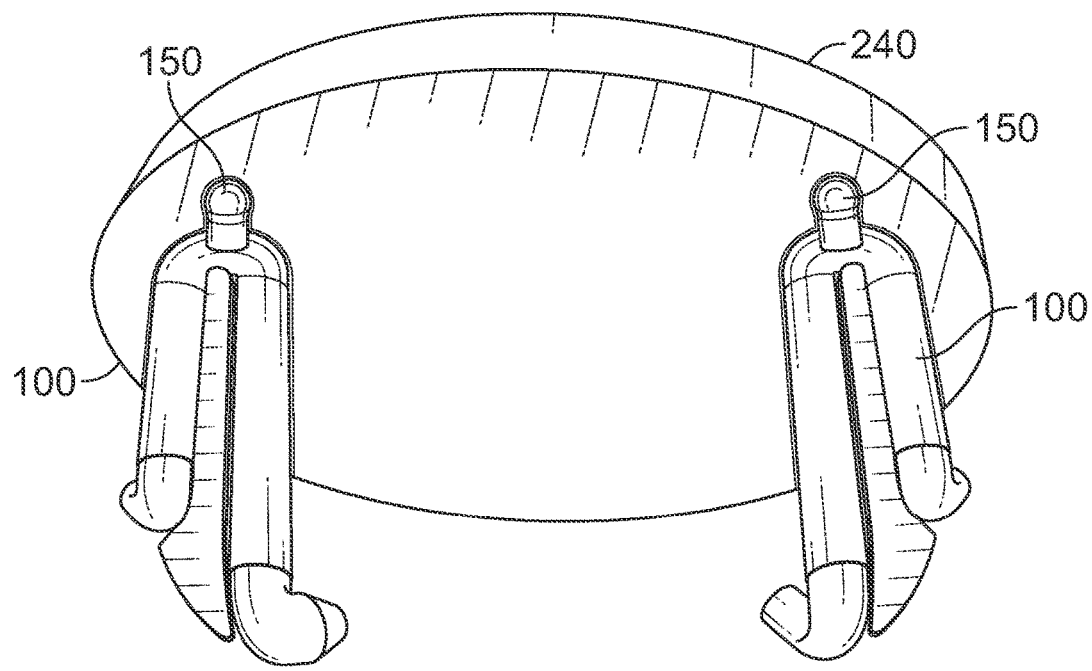
FIG. 17 illustrates an isometric front view of the headrest of FIG. 16 having the systems in stowed positions.

FIG. 16 illustrates an isometric front view of a headrest 240 including systems 100a and 100b for disinfecting air in deployed positions, according to an example of the present disclosure. FIG. 17 illustrates an isometric front view of the headrest 240 of FIG. 16 having the systems 100a and 100b in stowed positions. The headrest 240 shown in FIGS. 16 and 17 is similar to that shown in FIGS. 14 and 15, except that the systems 100a and 100b can be configured to downwardly pivot into the stowed positions, and upwardly pivot into the deployed positions.

Figure 18:
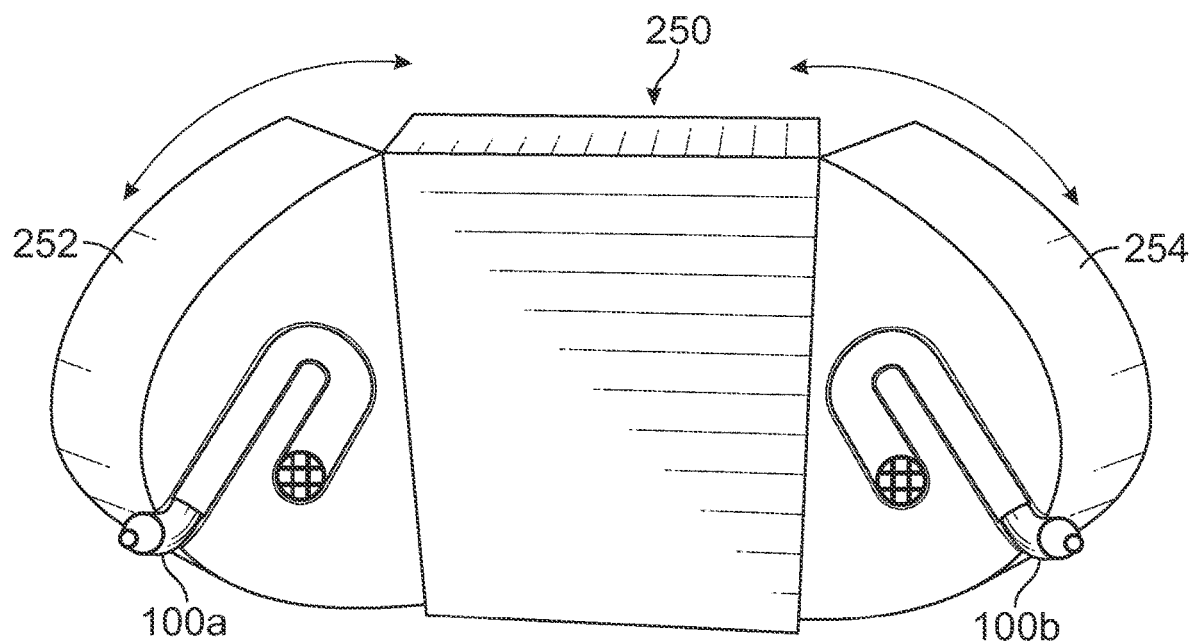
FIG. 18 illustrates an isometric front view of a headrest including systems for disinfecting air, according to an example of the present disclosure.

FIG. 18 illustrates an isometric front view of a headrest 250 including systems 100a and 100b for disinfecting air, according to an example of the present disclosure. The systems 100a and 100b can be configured as any of the systems 100 described herein. As shown, the systems 100a and 100b can be integrated into moveable side flaps 252 and 254 of the headrest 250.

Figure 19:
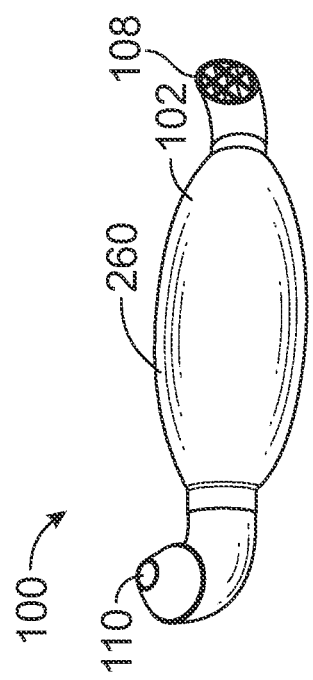
FIG. 19 illustrates an isometric view of a system for disinfecting air, according to an example of the present disclosure.

FIG. 19 illustrates an isometric view of a system 100 for disinfecting air, according to an example of the present disclosure. As shown, the duct 102 may not include a bend. Instead, the air outlet 110 can be distally located from the air inlet 108. The duct 102 can also include an expanded main body 260, which has a larger diameter than the air inlet 108 and the air outlet 110. The expanded main body 260 provides a larger UV irradiance zone, which increases air disinfection for a given input power. Any of the examples described herein can include a duct having an expanded main body 260, such as shown in FIG. 19. For example, the first and second segments of the duct 102 shown in FIG. 1 can include expanded main bodies.

Figure 20:
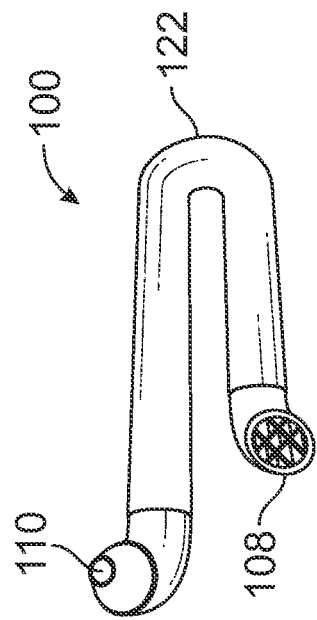
FIG. 20 illustrates an isometric view of a system for disinfecting air, according to an example of the present disclosure.

FIG. 20 illustrates an isometric view of a system 100 for disinfecting air, according to an example of the present disclosure. As shown, the duct 102 can include the bend 122. The duct 102 can include additional bends.

Figure 21:
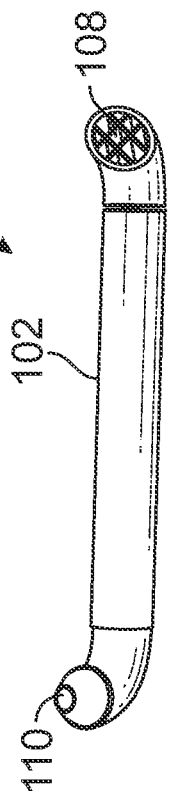
FIG. 21 illustrates an isometric view of a system for disinfecting air, according to an example of the present disclosure.

FIG. 21 illustrates an isometric view of a system 100 for disinfecting air, according to an example of the present disclosure. As shown, the duct 102 can include a straight main body that has a diameter that is the same, or substantially the same, as the air inlet 108.

Figure 22:
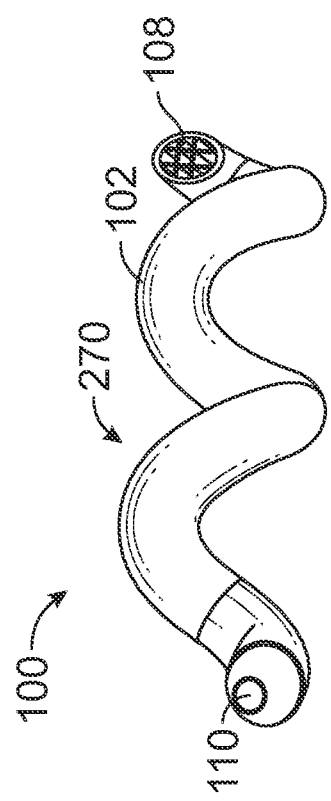
FIG. 22 illustrates an isometric view of a system for disinfecting air, according to an example of the present disclosure.

FIG. 22 illustrates an isometric view of a system for disinfecting air, according to an example of the present disclosure. As shown, the duct 102 can include a spiraled main body 270, which provides a longer path for air to travel and thereby be exposed to UV light therein.

Figure 23:
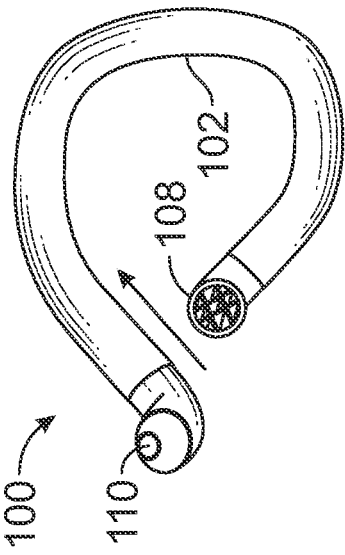
FIG. 23 illustrates an isometric view of a system for disinfecting air, according to an example of the present disclosure.

FIG. 23 illustrates an isometric view of a system 100 for disinfecting air, according to an example of the present disclosure. As shown, the duct 102 can have an irregularly-curved shape. The duct 102 can be sized and shaped as desired.

Figure 24:
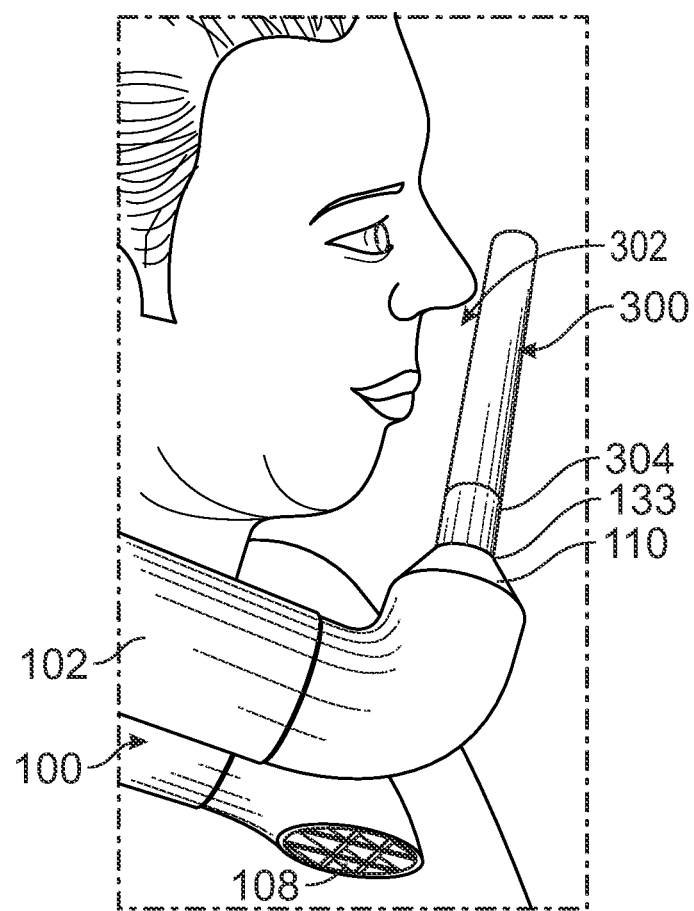
FIG. 24 illustrates an isometric view of a system for disinfecting air, according to an example of the present disclosure.

FIG. 24 illustrates an isometric view of a system 100 for disinfecting air, according to an example of the present disclosure. As shown, an outlet tube 300 (for example, a flexible hose) can extend from the nozzle 133 of the air outlet 110. The outlet tube 300 be permanently secured to the nozzle 133. Optionally, the outlet tube 300 can be removably secured to the nozzle 133, such as via a threadable interface, a snappable interface, an interference fit, or the like. In this manner, the outlet tube 300 can be a disposable tube that can be removably coupled to the air outlet 110.

The outlet tube 300 includes one or more air openings 302, such as a linear slot, which allow air to be expelled therefrom. A pivot joint 304 can couple the outlet tube 300 to the nozzle 133. The pivot joint 304 allows an individual to selectively adjust and orient the outlet tube 300, as desired. The pivot joint 304 allows an individual to control the direction of disinfected air.

Figure 25:
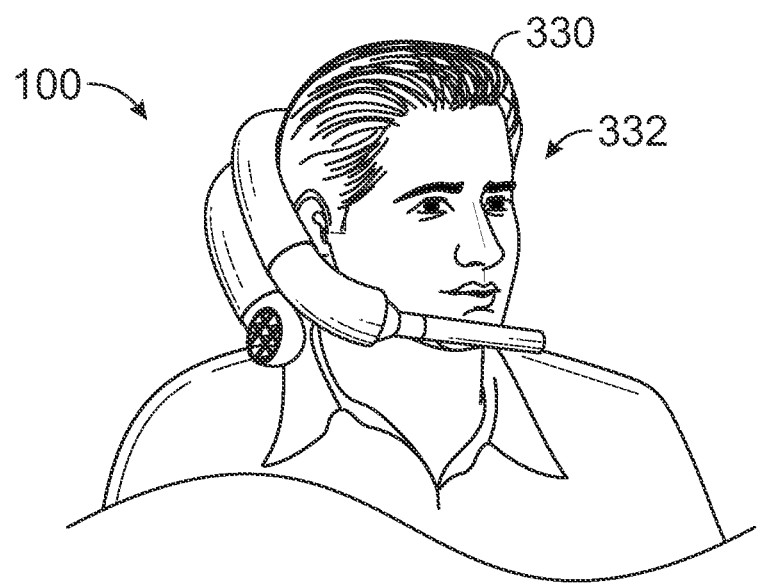
FIG. 25 illustrates an isometric front view of a system worn on a head of an individual, according to an example of the present disclosure.
Figure 26:
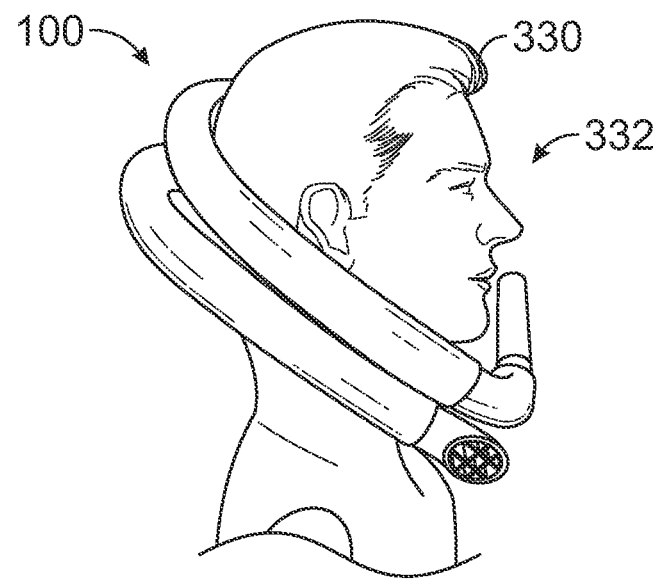
FIG. 26 illustrates an isometric side view of the system of FIG. 25 worn on the head of the individual.
Figure 27:
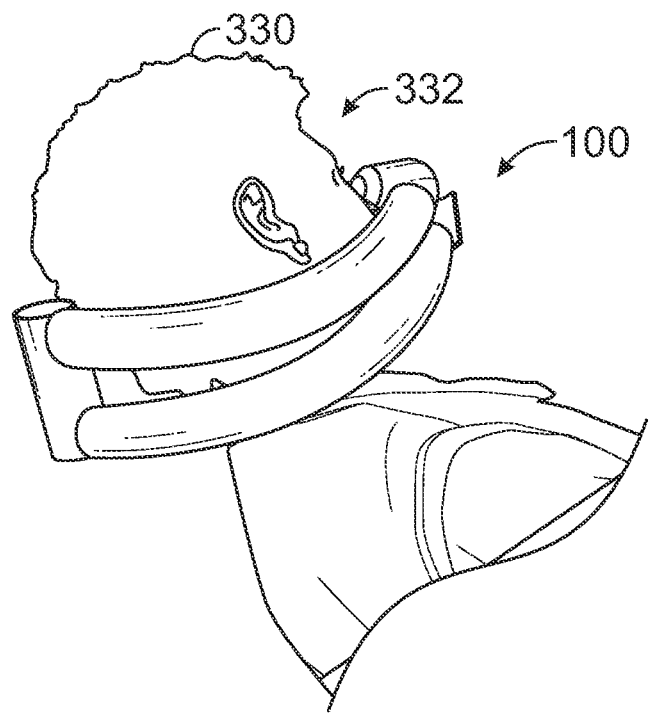
FIG. 27 illustrates an isometric rear view of the system of FIG. 25 worn on the head of the individual.

FIG. 25 illustrates an isometric front view of a system 100 worn on a head 330 of an individual 332, according to an example of the present disclosure. FIG. 26 illustrates an isometric side view of the system 100 of FIG. 25 worn on the head 330 of the individual 332. FIG. 27 illustrates an isometric rear view of the system 100 of FIG. 25 worn on the head 330 of the individual 332. The system 100 can be configured as any of those described herein. The system 100 can include one or more straps, loops, hooks, or the like that allow the system 100 to be worn on the head 330. In at least one example, the system 100 can be incorporated into a hood, headband, or the like that is worn by the individual 332. As another example, the system 100 can be supported by shoulders of the individual 332. As another example, the system 100 can partially loop around the head and/or neck of the individual 332.

Figure 28:
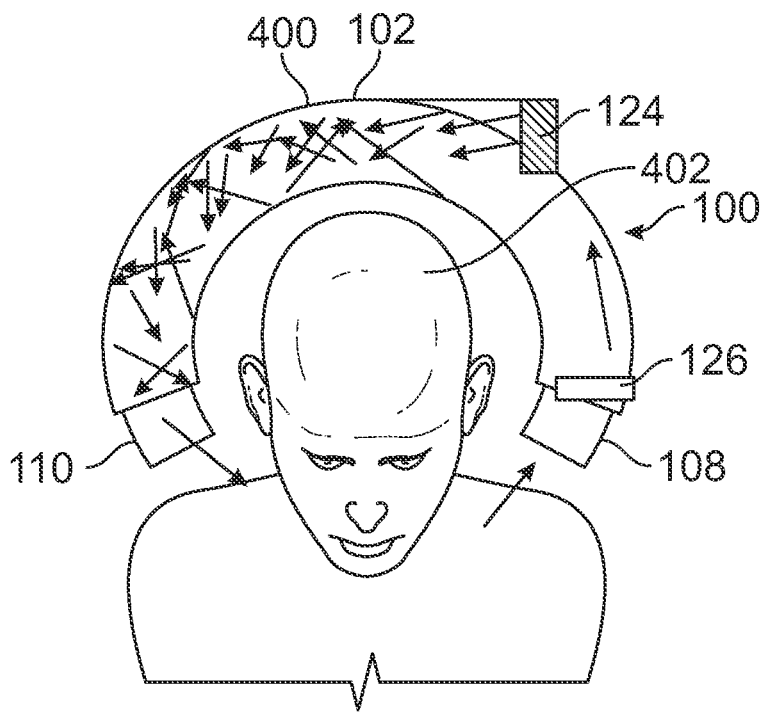
FIG. 28 illustrates a simplified internal view of a system for disinfecting air, according to an example of the present disclosure.

FIG. 28 illustrates a simplified internal view of a system 100 for disinfecting air, according to an example of the present disclosure. The duct 102 can have an arcuate main body 400 that is configured to extend around a portion of a head 402. The UV light emitter(s) 124 can be disposed within any portion of the duct 102. The blower 126 can be proximate to the air inlet 108. Optionally, the blower 126 can be within any other portion of the duct 102.

Figure 29:
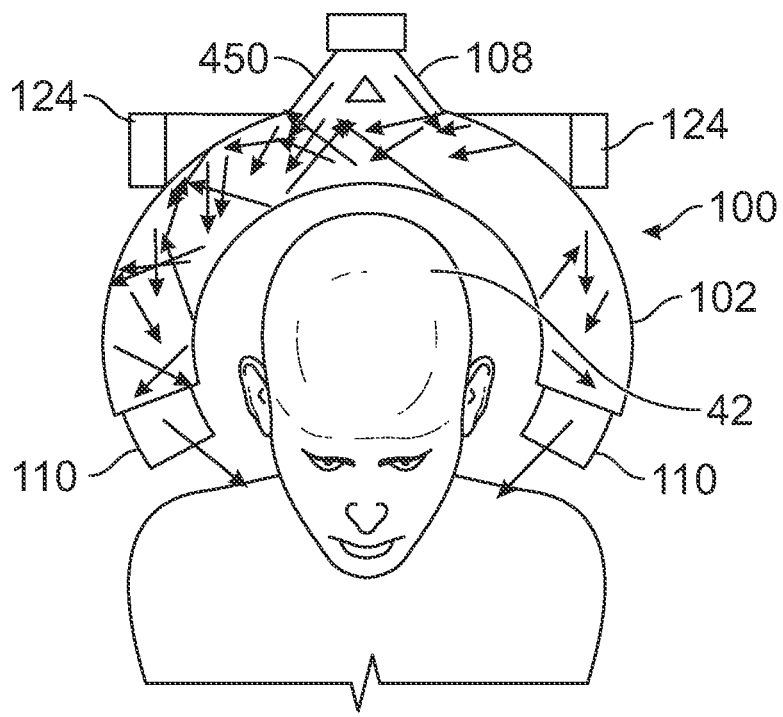
FIG. 29 illustrates a simplified internal view of a system for disinfecting air, according to an example of the present disclosure.

FIG. 29 illustrates a simplified internal view of a system 100 for disinfecting air, according to an example of the present disclosure. In this example, the air inlet 108 can be proximate to a middle section 450 of the duct 102 behind the head 402. The duct 102 further includes two air outlets 110 at opposite ends that are configured to be proximate to opposite sides of the head 402. The blower 126 can be disposed proximate to the air inlet 108. Multiple UV light emitters 124 can be used.

Figure 30:
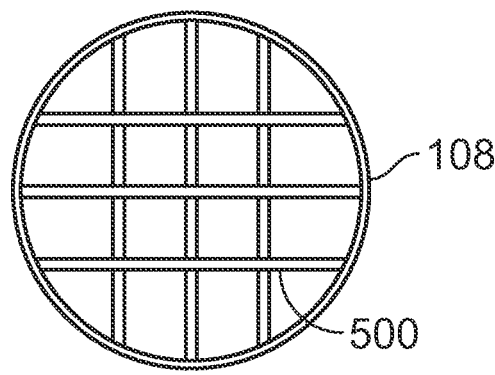
FIG. 30 illustrates a front view of an air inlet, according to an example of the present disclosure.

FIG. 30 illustrates a front view of the air inlet, 108 according to an example of the present disclosure. The air inlet 108 can include a screen 500, such as a metal mesh screen, disposed therein. The air outlet 110 can also include a screen 500. The screen 500 prevents foreign object debris from passing into the air inlet 108 (and/or the air outlet 110).

Figure 31:
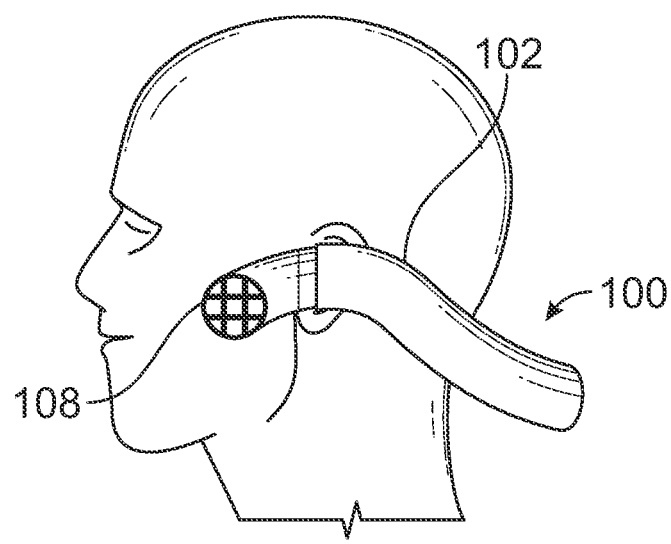
FIG. 31 illustrates a side view of a system for disinfecting air, according to an example of the present disclosure.

FIG. 31 illustrates a side view of a system 100 for disinfecting air, according to an example of the present disclosure. As shown, the duct 102 can be sized to rise above a height of the air inlet 108 (or optionally, the air outlet 110) to prevent foreign object debris from passing into the duct 102.

Figure 32:
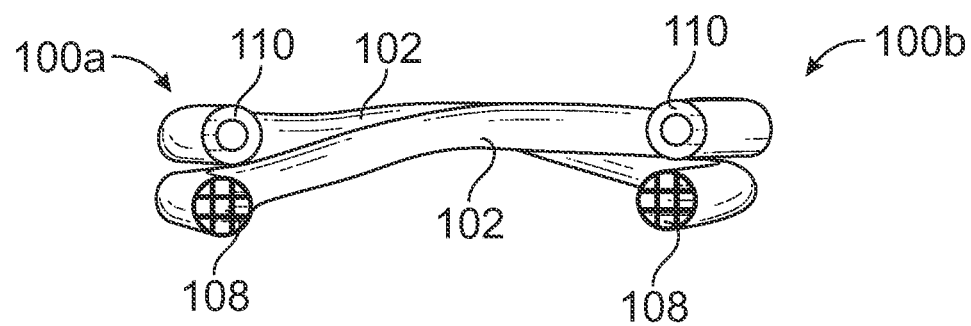
FIG. 32 illustrates an isometric front view of systems for disinfecting air, according to an example of the present disclosure.

FIG. 32 illustrates an isometric front view of systems 100*a* and 100*b* for disinfecting air, according to an example of the present disclosure. The systems 100*a* and 100*b* can be configured as any of those described herein. The systems 100*a* and 100*b* are configured to wrap around a head of an individual. The ducts 102 of the systems 100*a* and 100*b* are shaped such that the air inlet 108 of the system 100*a* is below the air outlet 110 of the system 100*b*, and the air inlet 108 of the system 100*b* is below air outlet 110 of the system 100*a*.

Figure 33:
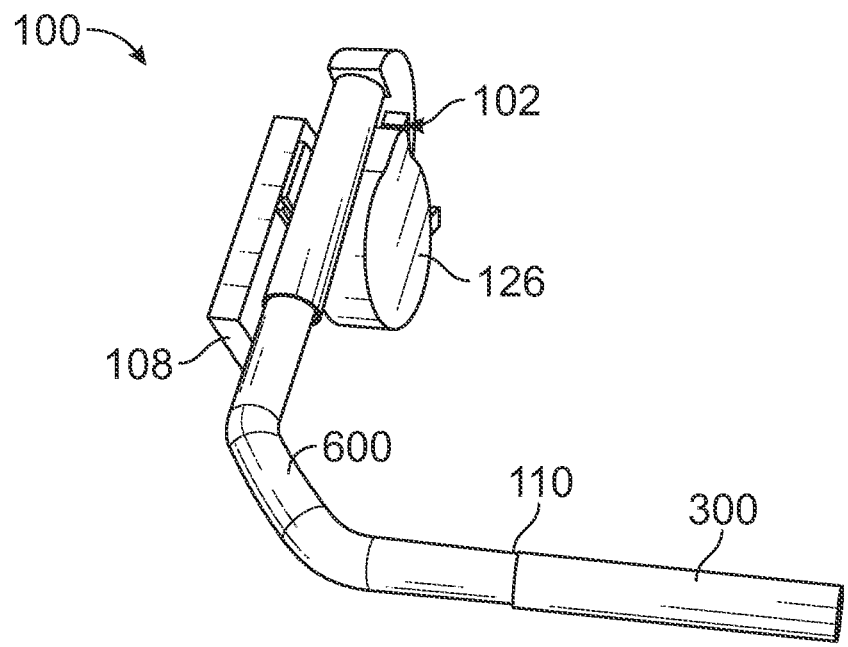
FIG. 33 illustrates an isometric first side view of a system for disinfecting air, according to an example of the present disclosure.
Figure 34:
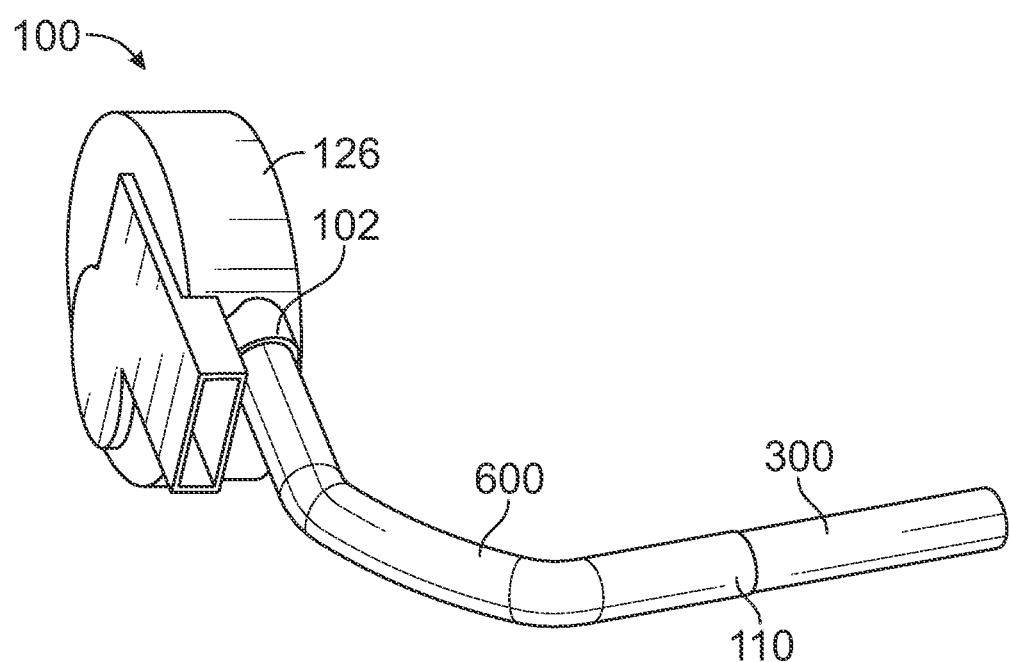
FIG. 34 illustrates an isometric second side of the system of FIG. 33.

FIG. 33 illustrates an isometric first side view of a system 100 for disinfecting air, according to an example of the present disclosure. FIG. 34 illustrates an isometric second side view of the system 100 of FIG. 33. As shown, the air inlet 108 is mounted to a side of the blower 126 and the duct 102, which provides the light pipe, as described herein. A flexible tube 600 extends from the duct 102, and provides the air outlet 110. An outlet tube 300 can extend from the air outlet 110, as described herein. Optionally, the flexible tube 300 can be a rigid conduit, such as a solid pipe.

Figure 35:
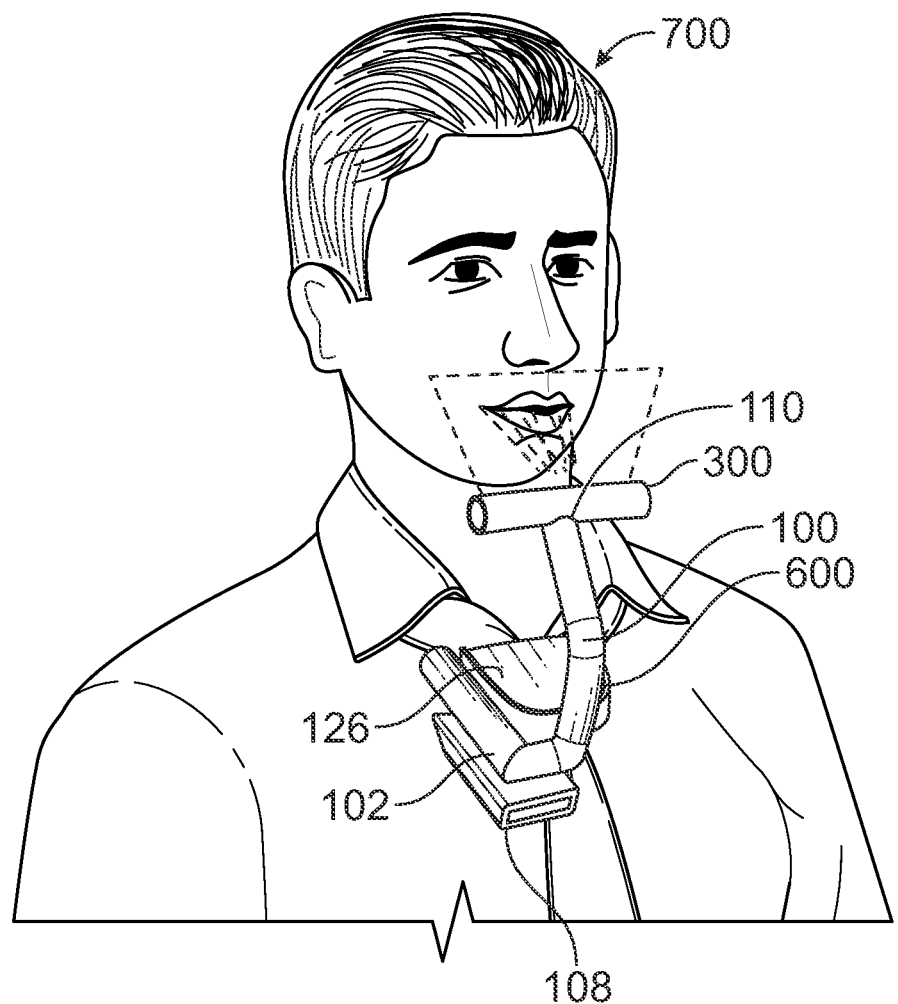
FIG. 35 illustrates an isometric front view of an individual wearing the system of FIGS. 33 and 34, according to an example of the present disclosure.

FIG. 35 illustrates an isometric front view of an individual 700 wearing the system 100 of FIGS. 33 and 34, according to an example of the present disclosure. The system 100 can include one or more features that allow the individual 700 to wear the system 100, as described herein. Optionally, the system 100 can be incorporated into a structure, such as a headrest, pillow, helmet, or the like.

The flexible tube 600 allows the individual 700 to move the outlet tube 300 to a desired position. Further, the outlet tube 300 can be pivoted, extended, and/or the like in relation to the air outlet 110.

Figure 36:
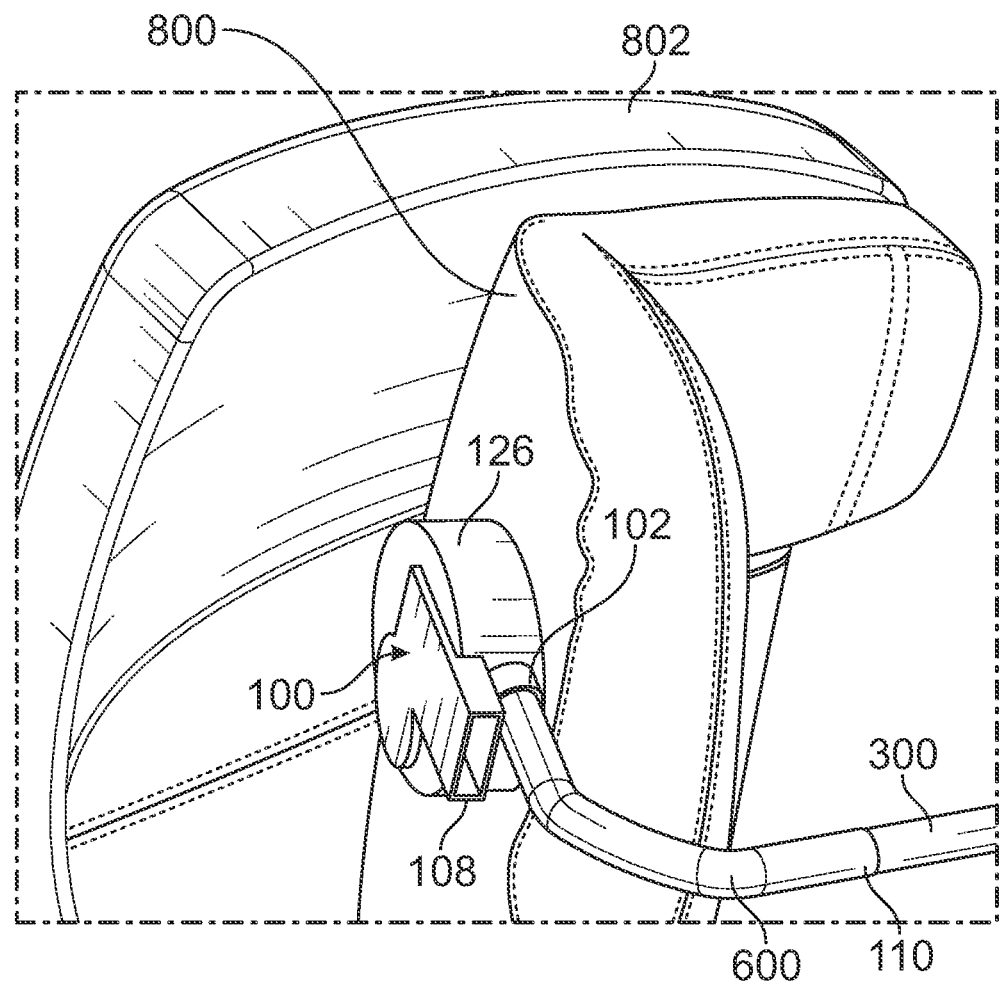
FIG. 36 illustrates a perspective view of the system of FIGS. 33 and 34 mounted to a side flap of a headrest, according to an example of the present disclosure.

FIG. 36 illustrates a perspective view of the system 100 of FIGS. 33 and 34 mounted to a side flap 800 of a headrest 802, according to an example of the present disclosure. As shown, the air inlet 108, the blower 126, and the duct 102 can be secured behind the side flap 800, and the flexible tube 600 extends in front of the side flap 800.

Figure 37:
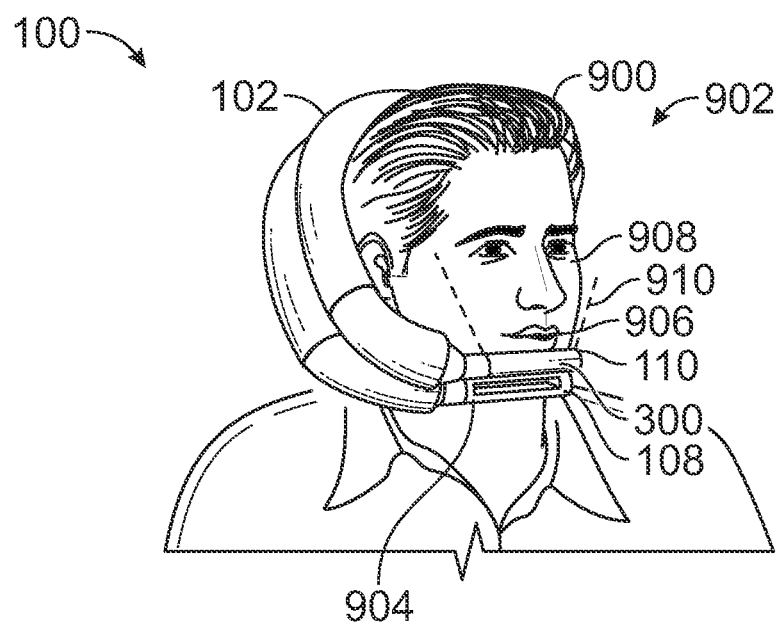
FIG. 37 illustrates an isometric front view of a system worn on a head of an individual, according to an example of the present disclosure.

FIG. 37 illustrates an isometric front view of a system 100 worn on a head 900 of an individual 902, according to an example of the present disclosure. As shown, the air inlet 108 is in close proximity to the air outlet 110. In particular, the air inlet 108 can be disposed below the air outlet 110. In at least one example, the air inlet 108 includes an inlet tube 904 that is coupled to the duct 102. Similarly, the air outlet 110 includes an outlet tube 300 to the duct 102. The air inlet 108 and the air outlet 110 can be fixed in relation to the duct 102. As another example, the air inlet 108 and the air outlet 110 can be pivotally secured to the duct 102, thereby allowing adjustable positioning of the outlet tube 300 and the inlet tube 904.

The inlet tube 904 and the outlet tube 300 can abut against one another or be separated a distance (such as 2 inches or less). In at least one example, the inlet tube 904 is disposed below the outlet tube 300. The inlet tube 904 and the outlet tube 300 can be configured to be disposed in front of and/or below a mouth 906 of the individual 902. The air outlet 110 can be positioned to discharge disinfected air upwardly toward the mouth 906 and face 908 of the individual 902, thereby providing an air curtain 910 that provides a barrier in front of the face 908. In this manner, the air curtain 910 reduces a potential of exhaled air and/or droplets from the mouth 906 of the individual 902 from passing toward others. Therefore, the system 100 protects the individual 902 by disinfecting air that is inhaled by the individual 902, and others via the air curtain 910 providing a protective barrier that reduces transmission of exhaled particles from the individual 902.

The outlet tube 300 and the inlet tube 904 as shown in FIG. 37 can be used with any of the examples shown and described with respect to FIGS. 1-36.

Figure 38:
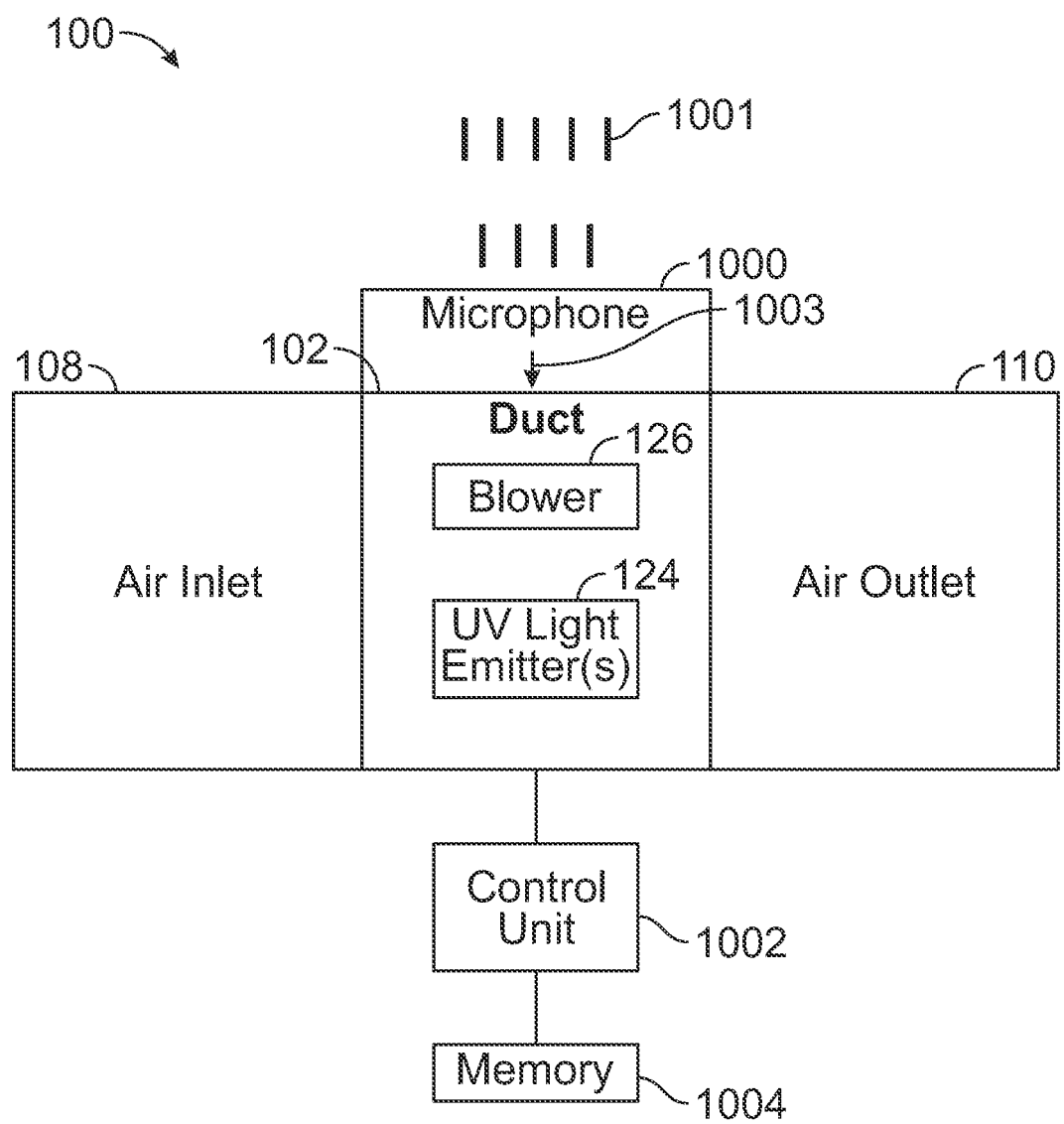
FIG. 38 illustrates a schematic block diagram of a system for disinfecting air, according to an example of the present disclosure.

FIG. 38 illustrates a schematic block diagram of a system 100 for disinfecting air, according to an example of the present disclosure. The system 100 includes the duct 102, the air inlet 108, and the air outlet 110, such as described above One or more UV light emitters 124 and the blower 126 are disposed in relation to the duct 102, as described above.

In at least one example, a sensor, such as a microphone 1000, is coupled to one or more of the duct 102, the air inlet 108, and/or the air outlet 110. For example, the microphone 1000 can be mounted to the duct 102 proximate to the air inlet 108 and/or the air outlet 110. As another example, the microphone 1000 is mounted to one or both of the air inlet 108 and/or the air outlet 110. The microphone 1000 is configured to detect sound as emitted by an individual. For example, the microphone 1000 is configured to detect sounds 1001 associated with breathing, speaking, and the like, and output audio signals 1003 indicative of the sounds 1001. Optionally, instead of a microphone, the sensor can be a pressure sensor that is configured to detect breathing through pressure detection. In such an example, the sensor can output pressure signals, instead of audio signals.

The system 100 also includes a control unit 1002 in communication with a memory 1004, such as through one or more wired or wireless connections. The control unit 1002 can be separate and distinct from the memory 1004. Optionally, the control unit 1002 can include the memory 1004.

The control unit 1002 and the memory 1004 are secured to one or more portions of the system 100. For example, the control unit 1002 and the memory 1004 can be mounted to an exterior portion of the duct 102. As another example, the control unit 1002 and the memory 1004 can be secured within the duct 102.

The control unit 1002 is in communication with the microphone 1000, the UV light emitter(s) 124, and the blower 126, such as through one or more wired or wireless connections. The control unit 1002 is configured to control operation of the UV light emitter(s) 124 and the blower 126 based on the audio signals 1003 received from the microphone 1000. The memory 1004 stores pre-programmed instructions for operating the UV light emitter(s) 124 and/or the blower 126 based on the audio signals 1003 output by the microphone 1000 and received by the control unit 1002.

The control unit 1002 is configured to recognize and differentiate the audio signals 1003 received from the microphone 1000. For example, based on preprogrammed data stored in the memory 1004, the control unit 1002 is configured to determine audio signals 1003 associated with inhalation of air, exhalation of air, and the like. In at least one example, the control unit 1002 is configured to determine a breathing rate of an individual based on the audio signals 1003 received from the microphone 1000. The control unit 1002 selectively controls the UV light emitters 124 and/or the blower 126 based on the audio signals received from the microphone 1000.

As an example, the microphone 1000 outputs the audio signals 1003 indicative of the sounds 1001 detected from an individual. The control unit 1002 receives the audio signals 1003 and determines a breathing rate and pattern of the individual. The control unit 1002 predicts when the individual inhales air based on the audio signals 1003 received from the microphone 1000. In response, the control unit 1002 increases power to the blower 126 to increase the air flow out of the air outlet 110 when the individual is breathing in air. As another example, the control unit 1002 increases power to the UV light emitter(s) 124 to provide increased UV disinfection when the individual is breathing in air. When the individual is not breathing in air or exhaling, the control unit 1002 reduces power to one or both of the UV light emitter(s) 124 and/or the blower 126 to conserve power. As another example, when the control unit 1002 determines that the individual is exhaling air, the control unit 1002 can increase power to the blower 126 to provide increased air flow, so as to provide a more robust air curtain in front of the face of the individual.

As described herein, in at least one example, the control unit 1002 is configured to increase power to one or both of the UV light emitter(s) 124 or the blower 126 when the signals indicate that an individual is or is about to inhale air discharged from the air outlet 110. Conversely, the control unit 1002 is configured to decrease power to one or both of the UV light emitter(s) 124 or the blower 126 when the signals indicate that the individual is not or is not about to inhale air discharged from the air outlet 110.

In at least one example, the control unit 1002 reduces power to the UV light emitter(s) 124 and/or the blower 126 when the audio signal 1003 is indicative of no breath intake. As such, the control unit 1002 can operate the components at reduced power when the individual is not inhaling air. As another example, the control unit 1002 can deactivate the components when the individual is not inhaling air.

As another example, the control unit 1002, based on data stored in the memory 1004, can determine when an individual is running or exerting increased amounts of energy, and selectively control the UV light emitter(s) 124 and/or the blower 126 in response thereto. For example, in response to receiving audio signals from the microphone 1000 indicative of the individual running, the control unit 1002 increases power to the UV light emitter(s) 124 to provide increased UV disinfection, and increases power to the blower 126 to provide increased air flow to the individual.

In at least one other example, the control unit 1002 can determine a breathing rate, and predict when an individual inhales and exhales air based on machine learning and/or artificial intelligence. For example, based on the audio signals 1003 received from the microphone 1000, the control unit 1002 can detect a pattern of sounds, and automatically make predictions regarding respiration of the individual based on the pattern.

In at least one example, the control unit 1002 determines breathing rate and intensity through the audio signals 1003 received from the microphone 1000 and selectively controls the UV light emitter(s) 124 and the blower 126 accordingly. The control unit 1002 uses artificial intelligence to monitor a breathing pattern and increases power to the UV light emitter(s) 124 and/or the blower 126 in advance of anticipated next breath.

Any of the examples described herein, such as shown and described with respect to FIGS. 1-37, can include the control unit 1002 in communication with the microphone 1000, the UV light emitter(s) 124, and the blower 126. The control unit 1002 receives signals, such as the audio signals 1003, from a sensor, such as the microphone 1000. The signals are indicative of breathing activity of the individual. The control unit 1002 operates one or both of the UV light emitter(s) 124 and/or the blower 126 responsive to the signals, such as the audio signals 1003, received from the sensor, such as the microphone 1000.

As described herein, the system 100 includes the duct 102 including an internal air passage (such as the internal air passage 114). One or more ultraviolet (UV) lights 124 are coupled to the duct 102. The one or more UV lights 124 are configured to emit UV light into air that passes through the internal air passage. An air inlet 108 is coupled to the duct 102. The air inlet 108 is in fluid communication with the internal air passage. An air outlet 110 is coupled to the duct 102. The air outlet 110 is in fluid communication with the internal air passage. A blower 126 is disposed within the duct 102. The blower 126 is configured to draw the air into the internal air passage through the air inlet 108, and discharge the air from the internal air passage through the air outlet 110. The air is disinfected within the internal air passage by the UV light emitted by the one or more UV lights 124. A sensor (such as the microphone 1000, a pressure sensor, or the like) is coupled to one or more of the duct 102, the air inlet 108, or the air outlet 110. The sensor is configured to output signals, such as may be indicative of breathing of an individual. A control unit 1002 is in communication with the one or more UV lights 124, the blower 126, and the sensor. The control unit 1002 is configured to receive the signals from the sensor and control one or both of the one or more UV lights 124 or the blower 126 based on the signals.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the control unit 1002 may be or include one or more processors that are configured to control operation, as described herein.

The control unit 1002 is configured to execute a set of instructions that are stored in one or more data storage units or elements (such as one or more memories), in order to process data. For example, the control unit 1002 may include or be coupled to one or more memories. The data storage units may also store data or other information as desired or needed. The data storage units may be in the form of an information source or a physical memory element within a processing machine.

The set of instructions may include various commands that instruct the control unit 1002 as a processing machine to perform specific operations such as the methods and processes of the various examples of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of examples herein may illustrate one or more control or processing units, such as the control unit 1002. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control unit 1002 may represent processing circuitry such as one or more of a field programmable gate array (FPGA), application specific integrated circuit (ASIC), microprocessor(s), and/or the like. The circuits in various examples may be configured to execute one or more algorithms to perform functions described herein. The one or more algorithms may include aspects of examples disclosed herein, whether or not expressly identified in a flowchart or a method.

Figure 39:
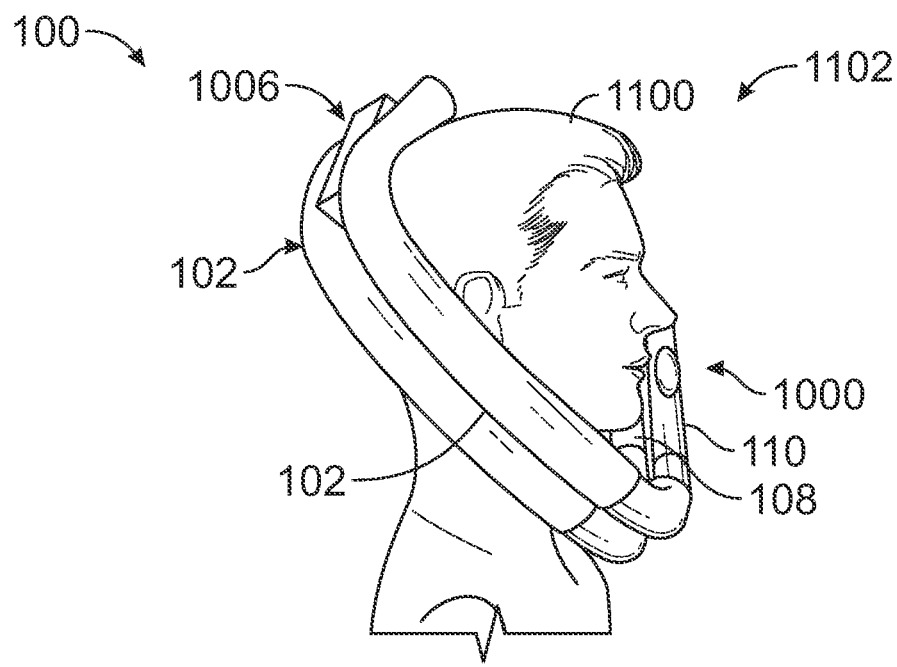
FIG. 39 illustrates an isometric top view of a system worn on a head of an individual, according to an example of the present disclosure.
Figure 40:
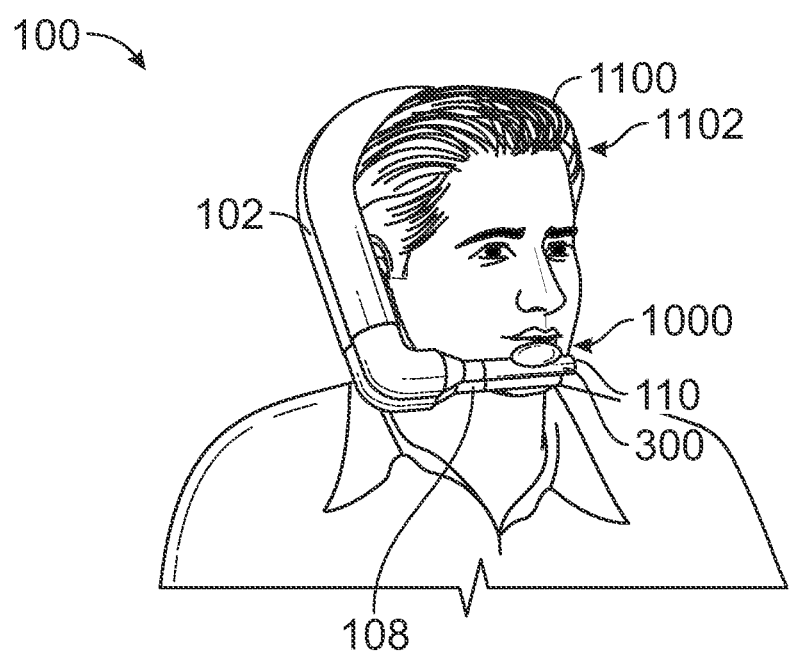
FIG. 40 illustrates an isometric front view of the system of FIG. 39.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program FIG. 39 illustrates an isometric top view of the system 100 worn on a head 1100 of an individual 1102, according to an example of the present disclosure. FIG. 40 illustrates an isometric front view of the system 100 of FIG. 39. Referring to FIGS. 39 and 40, the microphone 1000 can be secured to the air outlet 110. In at least one example, the microphone 1000 is mounted to an exterior or interior surface of the outlet tube 300. The microphone 1000 can be used with or without a headphone to predict a breathing pattern, for example.

The control unit 1002 can modulate power to the blower 126, based on breathing volume and/or intensity. For example, the control unit 1002 increased power to the blower 126 to increase fan speed (and therefore air volume) when hard breathing is detected and/or predicted, such as by an artificial intelligence algorithm. The power to the blower 126 can be modulated by listening to speech to increase fan speed when the speaking patter is predicted to include a breath. The power to the UV light emitter(s) 124 and/or the blower 126 can be modulated based on a predicted speaking volume, breathing rate, and/or the like.

The system 100 can also include a power source 1006. The power source 1006 can be or otherwise include one or more batteries. As another example, the system 100 can be powered via an electrical plug that is coupled to a power outlet, for example. The power source 1006 can be mounted to an exterior portion of the system 100, such as on an outer source of the duct 102. As another example, the power source 1006 can be mounted within the duct 102. Referring to FIGS. 38-40, the power source 1006 is in communication with the control unit 1002, the UV light emitter(s) 124, the blower 126, and the microphone 1000 such as through one or more wired or wireless connections. The power source 1006 provides power to the control unit 1002, the UV light emitter(s) 124, the blower 126, and the microphone 1000. In at least one example, the control unit 1002 is configured to control power from the power source 1006 to one or both of the UV light emitter(s) 124 and/or the blower 126 based on the audio signals 1003 received from the microphone 1000.

Figure 41:
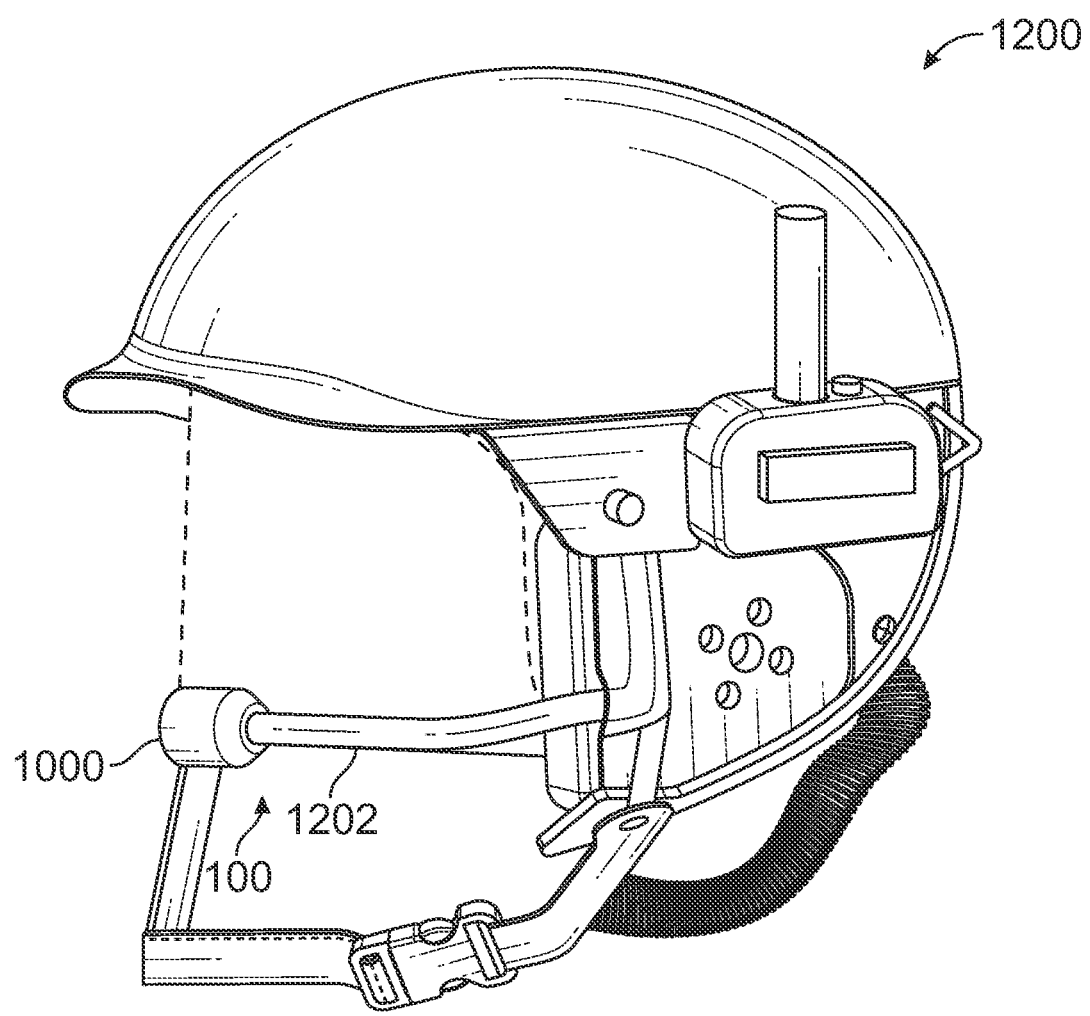
FIG. 41 illustrates a side view of a helmet including a system for disinfecting air, according to an example of the present disclosure.

FIG. 41 illustrates a side view of a helmet 1200 including a system 100 for disinfecting air, according to an example of the present disclosure. The helmet 1200 includes the microphone 1000, which can also be used in relation to communication. For example, the microphone 1000 can be used to communicate with other individuals, and also be used with respect to the system 100, as described herein. A conduit 1202 houses portions of the system 100 (such as the duct 102), as well as portions of a communication system (such as wiring that connects the microphone 1000 to a receiver and antenna). As such, the system 100 can be integrated into a helmet 1200 having a communication system, and the microphone 1000 can be used for different purposes, such as in relation the communication system and the system 100 for disinfecting air.

The system 100 for disinfecting air can be integrated into a mobile headset or helmet, such as the helmet 1200 shown in FIG. 41. As described herein, the control unit 1002 is configured to control operation of the system 100 based on the audio signals received from the microphone 1000, and can therefore conserve power consumed by components of the system 100. The air inlet 108 and the air outlet 110 can be in close proximity to one another, as shown and described with respect to FIGS. 37, 39, and 40, for example. By disposing the air outlet 108 in front of and/or below a mouth of the individual, discharged air from the air outlet 108 can form an air curtain in front of a face of the individual. The control unit 1002 can be configured to recognize and/or predict breathing rhythms of the individual via audio signals received from the microphone 1000, and can control power supplied to the UV light emitter(s) 124 and/or the blower 126 accordingly, which reduces overall power consumption and noise.

In at least one example, the systems and methods described herein are maskless. That is, the systems 100 do not include a mask that is worn around and over a mouth and/or nose of an individual. Such maskless systems do not visually restrict an individual. Alternatively, the air inlet 108 and/or the air outlet 110 can be in communication with a mask that is worn over a portion of the face.

The systems 100 provide disinfected air with lower power requirements in comparison to disinfection of larger spaces. The systems 100 consume less power and are quieter as compared to HEPA filter type systems. The systems 100 can be actively controlled, such as via the control unit 1002, and/or continuously operated. The systems 100 can be portable and battery operated. The systems 100 also eliminate or otherwise reduce UV exposure to skin and eyes. Also, the systems 100 provide increased disinfection of air next to an individual's nose and mouth.

Figure 42:
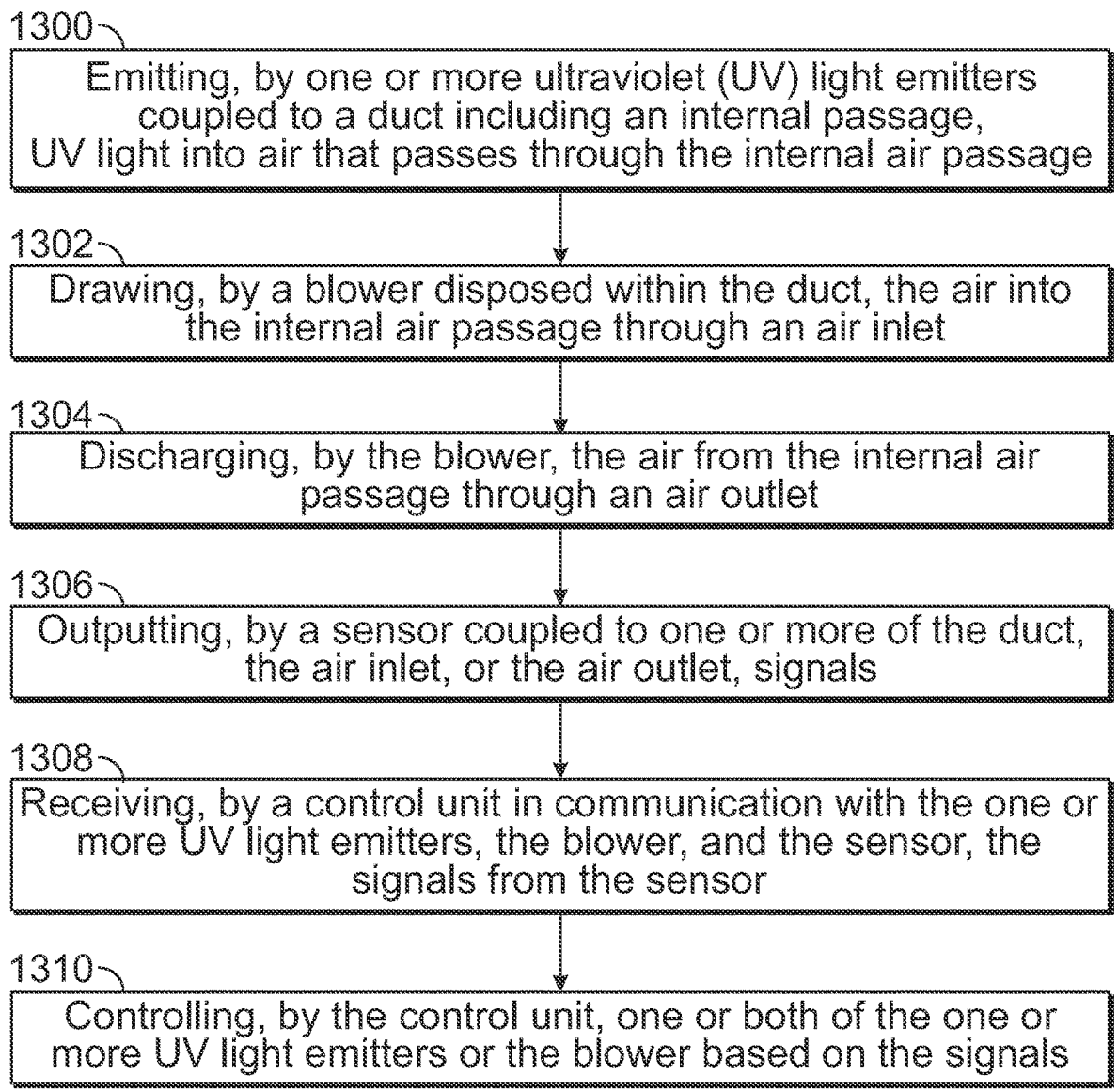
FIG. 42 illustrates a flow chart of a method for disinfecting air, according to an example of the present disclosure.

FIG. 42 illustrates a flow chart of a method for disinfecting air, according to an example of the present disclosure. The method includes emitting 1300, by one or more ultraviolet (UV) light emitters coupled to a duct including an internal passage, UV light into air that passes through the internal air passage; drawing 1302, by a blower coupled to the duct, the air into the internal air passage through an air inlet; discharging 1304, by the blower, the air from the internal air passage through an air outlet; outputting 1306, by a sensor coupled to one or more of the duct, the air inlet, or the air outlet, signals; receiving 1308, by a control unit in communication with the one or more UV light emitters, the blower, and the sensor, the signals from the sensor; and controlling 1310, by the control unit, one or both of the one or more UV light emitters or the blower based on the signals.

Further, the disclosure comprises examples according to the following clauses:

Clause 1. A system comprising:
a duct including an internal air passage;
one or more ultraviolet (UV) light emitters coupled to the duct, wherein the one or more UV light emitters are configured to emit UV light into air that passes through the internal air passage;
an air inlet coupled to the duct, wherein the air inlet is in fluid communication with the internal air passage;
an air outlet coupled to the duct, wherein the air outlet is in fluid communication with the internal air passage;
a blower coupled to the duct, wherein the blower is configured to draw the air into the internal air passage through the air inlet, and discharge the air from the internal air passage through the air outlet, and wherein the air is disinfected within the internal air passage by the UV light emitted by the one or more UV light emitters;
sensor coupled to one or more of the duct, the air inlet, or the air outlet, wherein the sensor is configured to output signals; and
a control unit in communication with the one or more UV light emitters, the blower, and the sensor, wherein the control unit is configured to receive the signals from the sensor and control one or both of the one or more UV light emitters or the blower based on the signals.

Clause 2. The system of Clause 1, wherein the air inlet is in close proximity to the air outlet.

Clause 3. The system of Clauses 1 or 2, wherein the air inlet is disposed below the air outlet.

Clause 4. The system of any of Clauses 1-3, wherein the air inlet or the air outlet are configured to be disposed one or both of below or in front of a mouth of an individual, wherein the air outlet is configured to discharge disinfected air upwardly toward the mouth to provide an air curtain in front of a face the individual.

Clause 5. The system of any of Clauses 1-4, wherein the sensor is a microphone, and wherein the signals are audio signals.

Clause 6. The system of any of Clauses 1-5, wherein the control unit is configured to determine a breathing rate of an individual based on the signals.

Clause 7. The system of any of Clauses 1-6, wherein the control unit is configured to control both the one or more UV light emitters and the blower based on the signals.

Clause 8. The system of any of Clauses 1-7, wherein the control unit is configured to increase power to one or both of the one or more UV light emitters or the blower when the signals indicate that an individual is or is about to inhale air discharged from the air outlet, and wherein the control unit is configured to decrease power to one or both of the one or more UV light emitters or the blower when the signals indicate that the individual is not or is not about to inhale air discharged from the air outlet.

Clause 9. The system of any of Clauses 1-8, further comprising a power source that supplies power to the one or more UV light emitters, the blower, the control unit, and the sensor.

Clause 10. The system of any of Clauses 1-9, further comprising a helmet, wherein the duct, the air inlet, the air outlet, and the control unit are coupled to the helmet.

Clause 11. A method comprising:
  emitting, by one or more ultraviolet (UV) light emitters coupled to a duct including an internal passage, UV light into air that passes through the internal air passage;
  drawing, by a blower coupled to the duct, the air into the internal air passage through an air inlet;
  discharging, by the blower, the air from the internal air passage through an air outlet;
  outputting, by a sensor coupled to one or more of the duct, the air inlet, or the air outlet, signals;
  receiving, by a control unit in communication with the one or more UV light emitters, the blower, and the sensor, the signals from the sensor; and
  controlling, by the control unit, one or both of the one or more UV light emitters or the blower based on the signals.

Clause 12. The method of Clause 11, wherein the air inlet is in close proximity to the air outlet.

Clause 13. The method of Clauses 11 or 12, wherein the air inlet is disposed below the air outlet.

Clause 14. The method of any of Clauses 11-13, wherein the air inlet or the air outlet are configured to be disposed one or both of below or in front of a mouth of an individual, wherein the air outlet is configured to discharge disinfected air upwardly toward the mouth to provide an air curtain in front of a face the individual.

Clause 15. The method of any of Clauses 11-14, wherein the sensor is a microphone, and wherein the signals are audio signals.

Clause 16. The method of any of Clauses 11-15, further comprising determining, by the control unit, a breathing rate of an individual based on the signals.

Clause 17. The method of any of Clauses 11-16, wherein said controlling comprises controlling both the one or more UV light emitters and the blower based on the signals.

Clause 18. The method of any of Clauses 11-17, wherein said controlling comprises:
  increasing power to one or both of the one or more UV light emitters or the blower when the signals indicate that an individual is or is about to inhale air discharged from the air outlet; and
  decreasing power to one or both of the one or more UV light emitters or the blower when the signals indicate that the individual is not or is not about to inhale air discharged from the air outlet.

Clause 19. The method of any of Clauses 11-18, further comprising coupling the duct, the air inlet, the air outlet, and the control unit to a helmet.

Clause 20. A system comprising:
  a duct including an internal air passage;
  one or more ultraviolet (UV) light emitters coupled to the duct, wherein the one or more UV light emitters are configured to emit UV light into air that passes through the internal air passage;
  an air inlet coupled to the duct, wherein the air inlet is in fluid communication with the internal air passage;
  an air outlet coupled to the duct, wherein the air outlet is in fluid communication with the internal air passage, wherein the air inlet is in close proximity to the air outlet, and wherein the air inlet is disposed below the air outlet;
  a blower coupled to the duct, wherein the blower is configured to draw the air into the internal air passage through the air inlet, and discharge the air from the internal air passage through the air outlet, and wherein the air is disinfected within the internal air passage by the UV light emitted by the one or more UV light emitters;
  a microphone coupled to one or more of the duct, the air inlet, or the air outlet, wherein the microphone is configured to output audio signals;
  a power source that supplies power to the one or more UV light emitters, the blower, the control unit, and the sensor; and
  a control unit in communication with the one or more UV light emitters, the blower, and the sensor, wherein the control unit is configured to determine a breathing rate of an individual based on the audio signals, and wherein the control unit is configured to receive the audio signals from the microphone and control the one or more UV light emitters and the blower based on the audio signals.

As described herein, examples of the present disclosure provide systems and methods for disinfecting air, such as within a confined space (for example, an internal cabin of a vehicle).

While various spatial and directional terms, such as top, bottom, lower, mid, lateral, horizontal, vertical, front and the like can be used to describe examples of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described examples (and/or aspects thereof) can be used in combination with each other. In addition, many modifications can be made to adapt a particular situation or material to the teachings of the various examples of the disclosure without departing from their scope. While the dimensions and types of materials described herein are intended to define the aspects of the various examples of the disclosure, the examples are by no means limiting and are exemplary examples. Many other examples will be apparent to those of skill in the art upon reviewing the above description. The scope of the various examples of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various examples of the disclosure, including the best mode, and also to enable any person skilled in the art to practice the various examples of the disclosure, including making and using any devices or systems and performing any incorporated methods. The patentable scope of the various examples of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system comprising:
   a duct including an internal air passage;
   one or more ultraviolet (UV) light emitters coupled to the duct, wherein the one or more UV light emitters are configured to emit UV light into air that passes through the internal air passage;
   an air inlet coupled to the duct, wherein the air inlet is in fluid communication with the internal air passage;
   an air outlet coupled to the duct, wherein the air outlet is in fluid communication with the internal air passage;
   a blower coupled to the duct, wherein the blower is configured to draw the air into the internal air passage through the air inlet, and discharge the air from the internal air passage through the air outlet, and wherein the air is disinfected within the internal air passage by the UV light emitted by the one or more UV light emitters;
   a sensor coupled to one or more of the duct, the air inlet, or the air outlet, wherein the sensor is configured to output signals; and
   a control unit in communication with the one or more UV light emitters, the blower, and the sensor, wherein the control unit is configured to:
      receive the signals from the sensor and control one or both of the one or more UV light emitters or the blower based on the signals,
      increase power to one or both of the one or more UV light emitters or the blower when the signals indicate that an individual is or is about to inhale air discharged from the air outlet, and
      decrease power to one or both of the one or more UV light emitters or the blower when the signals indicate that the individual is not or is not about to inhale air discharged from the air outlet.

2. The system of claim 1, wherein the duct comprises a first segment connected to a second segment through a bend.

3. The system of claim 1, wherein the air inlet is disposed below the air outlet.

4. The system of claim 1, wherein the air inlet or the air outlet are configured to be disposed one or both of below or in front of a mouth of an individual, wherein the air outlet is configured to discharge disinfected air upwardly toward the mouth to provide an air curtain in front of a face the individual.

5. The system of claim 1, wherein the sensor is a microphone, and wherein the signals are audio signals.

6. The system of claim 1, wherein the control unit is configured to determine a breathing rate of an individual based on the signals.

7. The system of claim 1, wherein the control unit is configured to control both the one or more UV light emitters and the blower based on the signals.

8. The system of claim 2, wherein the first segment is parallel with the second segment.

9. The system of claim 1, further comprising a power source configured to supply power to the one or more UV light emitters, the blower, the control unit, and the sensor.

10. The system of claim 1, further comprising a helmet, wherein the duct, the air inlet, the air outlet, and the control unit are coupled to the helmet.

11. A method for a system comprising:
   a duct including an internal air passage;
   one or more ultraviolet (UV) light emitters coupled to the duct, wherein the one or more UV light emitters are configured to emit UV light into air that passes through the internal air passage;
   an air inlet coupled to the duct, wherein the air inlet is in fluid communication with the internal air passage;
   an air outlet coupled to the duct, wherein the air outlet is in fluid communication with the internal air passage;
   a blower coupled to the duct, wherein the blower is configured to draw the air into the internal air passage through the air inlet, and discharge the air from the internal air passage through the air outlet, and wherein the air is disinfected within the internal air passage by the UV light emitted by the one or more UV light emitters;
   a sensor coupled to one or more of the duct, the air inlet, or the air outlet, wherein the sensor is configured to output signals; and
   a control unit in communication with the one or more UV light emitters, the blower, and the sensor, wherein the control unit is configured to:
      receive the signals from the sensor and control one or both of the one or more UV light emitters or the blower based on the signals,
      increase power to one or both of the one or more UV light emitters or the blower when the signals indicate that an individual is or is about to inhale air discharged from the air outlet, and
      decrease power to one or both of the one or more UV light emitters or the blower when the signals indicate that the individual is not or is not about to inhale air discharged from the air outlet,
   the method comprising:
      emitting, by the one or more UV light emitters coupled to the duct including the internal passage, the UV light into the air that passes through the internal air passage;
      drawing, by the blower coupled to the duct, the air into the internal air passage through the air inlet;
      discharging, by the blower, the air from the internal air passage through the air outlet;
      outputting, by the sensor coupled to one or more of the duct, the air inlet, or the air outlet, signals;
      receiving, by the control unit in communication with the one or more UV light emitters, the blower, and the sensor, the signals from the sensor; and controlling, by the control unit, one or both of the one or more UV light emitters or the blower based on the signals, wherein said controlling comprises:
   increasing power to one or both of the one or more UV light emitters or the blower when the signals indicate that the individual is or is about to inhale air discharged from the air outlet; and
   decreasing power to one or both of the one or more UV light emitters or the blower when the signals indicate that the individual is not or is not about to inhale air discharged from the air outlet.

12. The method of claim 11, wherein the duct comprises a first segment connected to a second segment through a bend, and wherein the first segment is parallel with the second segment.

13. The method of claim 11, wherein the air inlet is disposed below the air outlet.

14. The method of claim 11, wherein the air inlet or the air outlet are configured to be disposed one or both of below or in front of a mouth of an individual, wherein the air outlet is configured to discharge disinfected air upwardly toward the mouth to provide an air curtain in front of a face the individual.

15. The method of claim 11, wherein the sensor is a microphone, and wherein the signals are audio signals.

16. The method of claim 11, further comprising determining, by the control unit, a breathing rate of an individual based on the signals.

17. The method of claim 11, wherein said controlling comprises controlling both the one or more UV light emitters and the blower based on the signals.

18. The method of claim 11, further comprising coupling the duct, the air inlet, the air outlet, and the control unit to a helmet.

19. A system comprising:
   a duct including an internal air passage;
   one or more ultraviolet (UV) light emitters coupled to the duct, wherein the one or more UV light emitters are configured to emit UV light into air that passes through the internal air passage;
   an air inlet coupled to the duct, wherein the air inlet is in fluid communication with the internal air passage;
   an air outlet coupled to the duct, wherein the air outlet is in fluid communication with the internal air passage, wherein the air inlet is disposed below the air outlet;
   a blower coupled to the duct, wherein the blower is configured to draw the air into the internal air passage through the air inlet, and discharge the air from the internal air passage through the air outlet, and wherein the air is disinfected within the internal air passage by the UV light emitted by the one or more UV light emitters;
   a microphone coupled to one or more of the duct, the air inlet, or the air outlet, wherein the microphone is configured to output audio signals;
   a power source; and
   a control unit in communication with the one or more UV light emitters, the blower, and the microphone, wherein the control unit is configured to:
     determine a breathing rate of an individual based on the audio signals,
     receive the audio signals from the microphone,
     increase power to one or both of the one or more UV light emitters or the blower when the audio signals indicate that an individual is or is about to inhale air discharged from the air outlet, and
     decrease power to one or both of the one or more UV light emitters or the blower when the audio signals indicate that the individual is not or is not about to inhale air discharged from the air outlet.

20. The system of claim 19, wherein the duct comprises a first segment connected to a second segment through a bend, and wherein the first segment is parallel with the second segment.

* * * * *